United States Patent
Foster et al.

(10) Patent No.: US 11,702,680 B2
(45) Date of Patent: *Jul. 18, 2023

(54) **MATERIALS AND METHODS FOR CONTROLLING PHA BIOSYNTHESIS IN PHA-GENERATING SPECIES OF THE GENERA *RALSTONIA* OR *CUPRIAVIDUS* AND ORGANISMS RELATED THERETO**

(71) Applicant: INV Nylon Chemicals Americas, LLC, Wilmington, DE (US)

(72) Inventors: Alexander Brett Foster, Redcar (GB); Cristina Serrano Amatriain, Redcar (GB); Gary J. Smith, Redcar (GB); Paul Sheldon Pearlman, Thornton, PA (US); Mark Paul Taylor, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,155

(22) Filed: Apr. 30, 2019

(65) Prior Publication Data

US 2019/0338320 A1    Nov. 7, 2019

Related U.S. Application Data

(60) Provisional application No. 62/665,751, filed on May 2, 2018.

(51) Int. Cl.
| | | |
|---|---|---|
| *C12P 7/625* | (2022.01) | |
| *C12N 1/20* | (2006.01) | |
| *C12N 9/04* | (2006.01) | |
| *C12N 9/10* | (2006.01) | |
| *C12N 9/88* | (2006.01) | |
| *C12P 7/04* | (2006.01) | |
| *C12P 7/06* | (2006.01) | |
| *C12P 7/42* | (2006.01) | |

(52) U.S. Cl.
CPC .............. *C12P 7/625* (2013.01); *C12N 1/20* (2013.01); *C12N 9/0006* (2013.01); *C12N 9/1029* (2013.01); *C12N 9/13* (2013.01); *C12N 9/88* (2013.01); *C12P 7/04* (2013.01); *C12P 7/065* (2013.01); *C12P 7/42* (2013.01); *C12Y 101/01001* (2013.01); *C12Y 203/01016* (2013.01); *C12Y 208/03015* (2013.01); *C12Y 401/01004* (2013.01); *C12N 2500/02* (2013.01); *C12N 2500/05* (2013.01); *C12N 2500/12* (2013.01); *C12N 2500/24* (2013.01)

(58) Field of Classification Search
CPC .. C12P 7/625; C12P 7/04; C12P 7/065; C12P 7/42; C12N 1/20; C12N 9/0006; C12N 9/1029; C12N 9/13; C12N 9/88; C12N 2500/02; C12N 2500/05; C12N 2500/12; C12N 2500/24; C12Y 101/01001; C12Y 203/01016; C12Y 208/03015; C12Y 401/01004
USPC ......................................................... 435/135
See application file for complete search history.

(56) References Cited

U.S. PATENT DOCUMENTS

| | | | |
|---|---|---|---|
| 3,957,876 A | 5/1976 | Rapoport et al. | |
| 4,554,101 A | 11/1985 | Hopp | |
| 6,207,217 B1 | 3/2001 | Peoples et al. | |
| 6,888,034 B1 | 5/2005 | Landray et al. | |
| 7,384,783 B2 * | 6/2008 | Kunas ..................... | B01F 7/001 435/289.1 |
| 8,603,518 B2 | 12/2013 | Boon et al. | |
| 8,809,027 B1 | 8/2014 | Lynch et al. | |
| 8,986,960 B2 | 3/2015 | Sichwart | |
| 9,221,737 B2 | 12/2015 | Valdez | |
| 9,580,733 B2 | 2/2017 | Botes et al. | |
| 9,637,764 B2 | 5/2017 | Botes et al. | |
| 9,650,653 B2 | 5/2017 | Pearlman et al. | |
| 9,862,973 B2 | 1/2018 | Botes et al. | |
| 9,920,339 B2 | 3/2018 | Kadi et al. | |
| 10,072,150 B2 | 9/2018 | Conradie et al. | |
| 10,196,657 B2 | 2/2019 | Pearlman et al. | |
| 10,577,634 B2 | 3/2020 | Pearlman et al. | |
| 10,975,363 B2 | 4/2021 | Foster et al. | |
| 2002/0192786 A1 | 12/2002 | Yamada et al. | |
| 2005/0181499 A1 | 8/2005 | Brahmbhatt | |
| 2007/0264688 A1 | 11/2007 | Venter et al. | |
| 2007/0269862 A1 | 11/2007 | Glass et al. | |

(Continued)

FOREIGN PATENT DOCUMENTS

| | | |
|---|---|---|
| CN | 102459579 A | 5/2012 |
| CN | 106795537 A | 5/2017 |

(Continued)

OTHER PUBLICATIONS

Girdhar et al., Process Parameters for Influencing Polyhyroxyalkanoate Producing Bacterial Factories: An Overview, J. Pet. Environ. Biotechnol. 2013, 4:5.*

(Continued)

*Primary Examiner* — Jennifer M. H. Tichy

(57) ABSTRACT

Provided herein are methods for generating cellular biomass in continuous aerobic fermentation systems. The biomass yield, and the concentration of polyhydroxyalkanoate within the biomass, are each directed to advantageous levels by operating the continuous fermentation system under particular nutrient limitation conditions. Also provided are biomass produced using the provided methods, and animal feed compositions including the provided biomass.

18 Claims, No Drawings

(56) References Cited

U.S. PATENT DOCUMENTS

| | | | |
|---|---|---|---|
| 2010/0120104 A1 | 5/2010 | Reed | |
| 2011/0125118 A1 | 5/2011 | Lynch | |
| 2011/0171702 A1 | 7/2011 | Reinecke et al. | |
| 2012/0003706 A1 | 1/2012 | Hickey | |
| 2012/0064622 A1* | 3/2012 | Fischer | C12P 5/00 435/348 |
| 2012/0295334 A1 | 11/2012 | Brahmbhatt | |
| 2013/0034884 A1 | 2/2013 | Burgard et al. | |
| 2013/0065285 A1 | 3/2013 | Sefton | |
| 2013/0177957 A1 | 7/2013 | Du et al. | |
| 2013/0189763 A1 | 7/2013 | Dalla-Betta et al. | |
| 2013/0323714 A1 | 12/2013 | Cheng et al. | |
| 2014/0248687 A1 | 9/2014 | Kelly et al. | |
| 2015/0132815 A1 | 5/2015 | Hickey | |
| 2015/0315599 A1* | 11/2015 | Shetty | C12N 15/52 435/6.18 |
| 2016/0176813 A1 | 6/2016 | Valdez | |
| 2016/0222420 A1 | 8/2016 | Botes | |
| 2017/0107474 A1 | 4/2017 | Farmer et al. | |
| 2017/0159082 A1 | 6/2017 | Conradie et al. | |
| 2017/0218406 A1 | 8/2017 | Conradie et al. | |
| 2018/0023088 A1 | 1/2018 | Van Eck Conradie et al. | |
| 2018/0023103 A1 | 1/2018 | Foster et al. | |
| 2018/0023104 A1 | 1/2018 | Cartman et al. | |
| 2018/0100160 A1 | 4/2018 | Bawdon et al. | |
| 2018/0327705 A1 | 11/2018 | Matsuka et al. | |
| 2019/0124947 A1 | 5/2019 | Pearlman et al. | |
| 2019/0300838 A1 | 10/2019 | Smith et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |
| 2019/0352674 A1 | 11/2019 | Foster et al. | |
| 2019/0352682 A1 | 11/2019 | Foster et al. | |
| 2019/0359957 A1 | 11/2019 | Foster et al. | |

FOREIGN PATENT DOCUMENTS

| | | |
|---|---|---|
| CN | 107849300 A | 3/2018 |
| EP | 0995490 A2 | 4/2000 |
| EP | 1728853 A1 | 12/2006 |
| EP | 1938892 A1 | 7/2008 |
| EP | 3399015 A1 | 11/2018 |
| JP | S49124358 A | 11/1974 |
| JP | 2007185133 A | 7/2007 |
| JP | 2009225662 A | 10/2009 |
| JP | 2013179909 A | 9/2013 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |
| WO | 2015117019 A1 | 8/2015 |
| WO | 2015149147 A1 | 10/2015 |
| WO | 2015195654 A1 | 12/2015 |
| WO | 2017165244 A1 | 9/2017 |
| WO | 2018005770 A2 | 1/2018 |
| WO | 2018022595 A1 | 2/2018 |
| WO | 2018022633 A1 | 2/2018 |
| WO | 2018106549 | 6/2018 |
| WO | 2018106549 A1 | 6/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Atlic et al., "Continuous Production of Poly([R]-3-Hydroxybutyrate) by Cupriavidus Necator in a Multistage Bioreactor Cascade", Appl Microbiol Biotechnology, vol. 91, 2011, pp. 295-304.

Byrd et al., "Bacterial Control of Agromyces Ramosus in Soil", Canadian Journal of Microbiology, vol. 31, No. 12, 1985, pp. 1157-1163.

Horvat et al., "Mathematical Modelling and Process Optimization of a Continuous 5-Stage Bioreactor Cascade for Production of Poly[-(R)-3-Hydroxybutyrate] by Cupriavidus Necator", Bioprocess Biosyst Eng, vol. 36, 2013, pp. 1235-1250.

Makkar et al., "*Cupriavidus necator* Gen. Nov., Sp. Nov.: A Nonobligate Bacterial Predator of Bacteria in Soil", International Journal of Systematic Bacteriology, vol. 37, No. 4, Oct. 1987, pp. 323-326.

Raberg et al., "A Closer Look on the Polyhydroxybutyrate- (PHB-) Negative Phenotype of Ralstonia Eutropha PHB-4", Plos One, vol. 9, No. 5, May 2014, pp. 1-11.

RUSSELL, "The Energy Spilling Reactions of Bacteria and Other Organisms", Journal of Molecular Microbiology Biotechnology, vol. 13, No. 1, 2007, pp. 1-11.

Sillman et al., "Isolation of Nonobligate Bacterial Predators of Bacteria from Soil", Canadian Journal of Microbiology, vol. 32, No. 9, 1986, pp. 760-762.

Zeph et al., "Gram-Negative Versus Gram-Positive (Actinomycete) Nonobligate Bacterial Predators of Bacteria in Soil", Applied Environmental Microbiology, vol. 52, No. 4, Oct. 1986, pp. 819-823.

Alagesan, S., et al., "13C-assisted metabolic flux analysis to investigate heterotrophic and mixotrophic metabolism in Cupriavidus necator H16", Metabolomics, 2018, vol. 14, Issue 9, pp. 9.

Alagesan, S., et al., "Functional genetic elements for controlling gene expression in Cupriavidus necator H16", Applied and Environmental Microbiology,vol. 84, Oct. 2018 (Oct. 2018), pp. 1-17.

Anderson, A.J., et al., "Occurrence, metabolism, metabolic role, and industrial uses of bacterial polyhydroxyalkanoates". Microbiology Review, 1990, vol. 54, pp. 450-472.

Bramer, C.O., "The malate dehydrogenase of Ralstonia eutropha and functionality of the C(3)/C(4) metabolism in a Tn5-induced mdh mutant", FEMS Microbiol Letters, Jul. 2, 2002, vol. 212, Issue 2, pp. 159-164.

Brandt, U., et al., "Elevated poly(3-hydroxybutyrate) synthesis in mutants of Ralstonia eutropha HI6 defective in lipopolysaccharide biosynthesis" Applied Microbiology and Biotechnology, 2012, vol. 95, pp. 471-483.

Brigham, C.J., et al., "Correction for Whole-genome microarray and gene deletion studies reveal regulation of the polyhydroxyalkanoate production cycle by the stringent response in Ralstonia eutropha H16", Appl Environ Microbiol., 2017, vol. 83, Issue 15, pp. 1-2.

Brigham, C.J., et al., "Whole-genome microarray and gene deletion studies reveal regulation of the polyhydroxyalkanoate production cycle by the stringent response in Ralstonia eutropha HI6", Appl Environ Microbial., 2012, vol. 78, Issue 22, pp. 8033-8044.

Brown, D.R., et al., "Nitrogen stress response and stringent response are coupled in *Escherichia coli*", Nature Communications, 2014, vol. 5, 4115, pp. 8.

Bruland et al. "Unravelling the C3/C4 carbon metabolism in Ralstonia eutropha H16" Journal of Applied Microbiology 2010 109:79-90.

Chae, T.U., et al., "Metabolic engineering of *Escherichia coli*for the production of four-, five- and six-carbon lactarns Metabolic Engineering", Academic Press, Us, vol. 41 ,Apr. 5, 2017, pp. 82-91.

Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.

Chen, R., et al., "A highly active decarboxylating dehydrogenase with rationally inverted coenzyme specificity", PNAS, 1996, vol. 92, Issue 25, pp. 11666-11670.

Chen, R., et al. "Redesigning secondary structure to invert coenzyme specificity in isopropylmalate dehydrogenase" PNAS, 1996, vol. 93, pp. 12171-12176.

(56) References Cited

OTHER PUBLICATIONS

Choi, J.C., et al. "Modulation of 3-hydroxyvalerate molar fraction in poly(3-hydroxybutyrate-3- hydroxyvalerate) using Ralstonia eutropha transformant co-amplifying phbC and NADPH generation-related zwf genes", Enzyme and Microbial Technology, 2003, vol. 32, Issue 1, pp. 178-185.

Cramm, R. J. "Genomic view of energy metabolism in Ralstonia eutropha HI6", Journal of Molecular Microbiology and Biotechnology, 2009, vol. 16, pp. 38-52.

Darani, K.K., et al., "Simulation of bioreactors for poly(3-hydroxybutyrate) production from natural gas", Iranian Journal of Chemistry and Chemical Engineering, vol. 39, 2018, pp. 1-24.

Ding, H., et al., "Glycerol utilization by Rhizobium leguminosarum requires an ABC transporter and affects competition for nodulation", Microbiology, 2012, vol. 158, pp. 1369-1378.

Doberstein, C., et al., "Polythioester synthesis in Ralstonia eutropha H16: novel insights into 3,3'-thiodipropionic acid and 3,3'-dithiodipropionic acid catabolism" Journal of Biotechnology, 2014, vol. 184, pp. 187-198.

Du et al., "Effects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.

Eggers et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24,Dec. 2014, pp. 7702-7709.

Frng, Y., et al., "Tuning of acyl-ACP thioesterase activity directed for tailored fatty acid synthesis", Applied Microbiology And Biotechnology, Springer, De, vol. 102, No. 7 ,Feb. 22, 2018, pp. 3173-3182.

Gao, C., et al. "Lactate utilization is regulated by the FadR-type regulator LldR in Pseudomonas aeruginosa", Journal of Bacteriology, 2012, vol. 194, pp. 2687-2692.

Grousseau, E., et al., "Isopropanol production with engineered Cupriavidus necator as bioproduction platform" Appl Microbiol Biotechnol, 2014, vol. 98, pp. 4277-4290.

Gyaneshwar et al., "Sulfur and Nitrogen Limitation in *Escherichia coli* K-12: Specific Homeostatic Responses", Journal of Bacteriology, vol. 187, No. 3, Feb. 2005, pp. 1074-1090.

Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.

Hauryliuk, V., et al. "Recent functional insights into the role of (p)ppGpp in bacterial physiology", Nature Reviews Microbiology, 2015, vol. 13, pp. 298-309.

Haushalter, R.W., et al., "Production of Odd-Carbon Dicarboxylic Acids in *Escherichia coli* Using an Engineered Biotin-Fatty Acid Biosynthetic Pathway" Journal Of The American Chemical Society, vol. 139, No. 13 ,Mar. 21, 2017, pp. 4615-4618.

Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.

Hun-Suk Song et al: Enhanced isobutanolproduction from acetate by combinatorialoverexpression of acetyl-CoA synthetaseand anaplerotic enzymes in engineered*Escherichia coli*, Biotechnology and Bioengineering,vol. 115, May 2, 2018 (May 2, 2018), pp. 1971-1978.

Lenczak, J.L., et al., "High cell density strategy for poly(3-hydroxybutyrate) production by Cupriavidus necator", Brazilian Journal of Chemical Engineering, 2011, vol. 28, Issue 4, pp. 585-596.

Inoue, H., et al., "Biochemical and molecular characterization of the NAD(+)-dependent isocitrate dehydrogenase from the chemolithotrophAcidithiobacillus thiooxidans", FEMS Microbial Letters, 2002, vol. 214, Issue 1, pp. 127-132.

International Search Report and Written Opinion for International Application Serial No. PCT/US2019/025189, dated Jul. 2, 2019, pp. 12.

International Search Report and Written Opinion for International Application Serial No. PCT/US2019/025194, dated Aug. 22, 2019, pp. 24.

International Search Report and Written Opinion for International Application Serial No. PCT/US2019/025202, dated Jul. 30, 2019, pp. 15.

International Search Report and Written Opinion for International Application Serial No. PCT/US2019/025211, dated Jul. 29, 2019, pp. 16.

International Search Report and Written Opinion for International Application Serial No. PCT/US2019/025218, dated Sep. 5, 2019, pp. 17.

International Search Report and Written Opinion for International Application Serial No. PCT/US2019/029973 dated Jul. 23, 2019, dated Jul. 23, 2019, 5 pgs.

International Search Report and Written Opinion in PCT/US2019/029795 dated Jul. 11, 2019, pp. 10.

International Search Report and Written Opinion in PCT/US2019/029798 dated Sep. 12, 2019, pp. 19.

International Search Report and Written Opinion in PCT/US2019/029817 dated Sep. 23, 2019.

International Search Report and Written Opinion in PCT/US2019/029827 dated Sep. 23, 2019.

International Search Report and Written Opinion in PCT/US2019/029956 dated Aug. 13, 2019.

Invitation to Pay Additional Fees and, Where Applicable, Protest Fee in PCT/082019/029798 dated Jul. 22, 2019.

Invitation to Pay Additional Fees and, WhereApplicable, Protest Fee in PCT/US2019/029817 dated Aug. 1, 2019.

Invitation to Pay Additional Fees and, WhereApplicable, Protest Fee in PCT/US2019/029827 datedJul. 23, 2019.

Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.

Joris, Beld, et al., "Evolution of acyl-ACP thioesterases and [beta]-ketoacyl-ACP synthases revealed by protein-protein interactions", Journal Of Applied Phycology, vol. 26, No. 4 ,Nov. 22, 2013, pp. 1619-1629.

Juengert, J.R, et al., "Absence of ppGpp Leads to Increased Mobilization of Intermediately Accumulated Poly(3-Hydroxybutyrate) in Ralstonia eutropha HI6" Applied and Environmental Microbiology, 2017, vol. 83, Issue 13, pp. e00755-17.

Justyna Mozejko-Ciesielska et al: "Bacterial polyhydroxyalkanoates: Still fabulous ?", Microbiological Research, vol. 192, 2016, pp. 271-282.

Kaddor, C., et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbiol., 2011, vol. 77, pp. 3582-3590.

Silva, F., et al., "Impact of nitrogen feeding regulation on polyhydroxyalkanoates production by mixed microbial cultures", New Biotechnology, vol. 37, 2017, pp. 90-98.

Steinbuchel, A., et al., "A multifunctional fermentative alcohol dehydrogenase from the strict aerobe Alcaligenes eutrophus: purification and properties" Eur J Biochem, 1984, vol. 141, Issue 3, pp. 555-564.

Stokke, R., et al., "Biochemical characterization of isocitrate dehydrogenase from Methylococcus capsulatus reveals a unique NAD+-dependent homotetrameric enzyme" Arch Microbiol., 2007, vol. 187, Issue 5, pp. 361-370.

Sun, J., et al., "Involvement of glnB, glnZ, and glnD genes in the regulation of poly-3-hydroxybutyrate biosynthesis by ammonia in Azospirillum brasilense Sp7", Appl Environ. Microbiol, 2002, vol. 68, Issue 2, pp. 985-988.

Sun, J., et al., "The ntrB and ntrC genes are involved in the regulation of poly-3-hydroxybutyrate biosynthesis by ammonia in Azospirillum brasilense Sp7", Appl Environ. Microbiol., 2000, vol. 66, Issue 1, pp. 113-117.

Tan, Z., et al. "Activating phosphoenolpyruvate carboxylase and phosphoenolpyruvate carboxykinase in combination for improvement of succinate production" Appl. Environ. Microbiol, 2013, vol. 79, Issue 16, pp. 4838-4844.

(56) References Cited

OTHER PUBLICATIONS

Tanaka, K, et al., Production Of Poly (D-3-Hydr0xybutyrate) From CO2, H2, And O2 By High Cell Density Autotropic Cultivation Of Alcaligenes Eutrophus Biotechnology And Bioengineering, Wiley, vol. 45, No. 3, (Feb. 5, 1995), XP000489583 ,Feb. 5, 1995, 268-275.
Valderrama, J.A., et al., "AccR is a master regulator involved in carbon catabolite repression of the anaerobic catabolism of aromatic compounds in *Azoarcus* sp. CIB" Journal of Biological Chemistry, 2014, vol. 289, Issue 4, pp. 1892-1904.
Vemuri, G.N., et al., "Physiological response of central metabolism in *Escherichia coli* to deletion of pyruvate oxidase and introduction of heterologous pyruvate carboxylase" Biotechnology and Bioengineering, 2005, vol. 90, Issue 1 pp. 64-76.
Vollbrecht, D., et al., "Excretion of Metabolites by Hydrogen Bacteria I. Autotrophic and Heterotrophic Fermentations" European Journal of Applied Microbiology and Biotechnology, 1978, vol. 6, Issue 2, pp. 145-155.
Vollbrecht, D., et al., "Excretion of Metabolites by Hydrogen Bacteria II. Influence of Aeration, pH, Temperature, and Age of Cells", European Journal of Applied Microbiology and Biotechnology, 1978, vol. 6, Issue 2, pp. 157-166.
Vollbrecht, D., et al., "Excretion of Metabolites by hydrogen Bacteria III. D(-)-3-hydroxybutanoate", European J. Appl. Microbiol. Biotechnol., 1979, vol. 7, pp. 259-266.
Vollbrecht, D., et al., "Excretion of Metabolites by Hydrogen Bacteria IV. Respiration Rate-Dependent Formation of Primary Metabolites and of Poly-3-hydroxybutanoate", Eropean Journal of Applied Microbiology and Biotechnology, 1979, vol. 7, Issue 3, pp. 267-276.
Volodina, E., et al., "Characterization of propionate CoA-transferase from Ralstonia eutropha HI6", Appl Microbial Biotechnol., 2014, vol. 98, Issue 8, pp. 3579-3589.
Wang, F., et al., "Poly(3-Hydroxybutyrate) Production with High Productivity and High Polymer Content by a Fed-Bath Culture of Alcaligene lat us under Nitrogen Limitation", Applied and Environmental Microbiology, 1997, vol. 63, No. 9, pp. 3703-3706.
Wang, R., et al., "Isocitrate dehydrogenase from *Streptococcus mutans*: biochemical properties and evaluation of a putative phosphorylation site at Ser102" PLoS One, 2013, vol. 8, Issue 3, e58918.
Weiden et al., "Cation Transport in *Escherichia coli* Vii. Potassium Requirement for Phosphate Uptake", The Journal of General Physiology, vol. 50, No. 6, 1967, pp. 1641-1661.
Weinberg, Z., et al. "Identification of 22 candidate structured RNAs in bacteria using the Cmfinder comparative genomics pipeline" Nucleic Acids Research, 2007, vol. 35, pp. 4809-4819.
Winnen, B., et al., "The tripartite tricarboxylate transporter (TTT) family" Res. Microbial., 2003, vol. 154, Issue 7, pp. 457-465.
Wu, M-C., et al., "A Novel Type II NAD+-Specific Isocitrate Dehydrogenase from the Marine Bacterium *Congregibacter litoralis* KT71" PLoS One., 2015, vol. 10, Issue 5, pp. 1-17.
Youngquist et al., "Functional Genomics Analysis of Free Fatty Acid Production under Continuous PhosphateLimiting Conditions", J. Ind. Microbial. Biotechnol., vol. 44, May 2017, pp. 759-772.
Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.
Ziesack, M., et al., "Chimeric Fatty Acyl-Acyl Carrier Protein Thioesterases Provide Mechanistic Insight into Enzyme Specificity and Expression", Applied And Environmental Microbiology, vol. 84, No. 10,Mar. 16, 2018, pp. 12.
Non-Final office action received for U.S. Appl. No. 16/399,145, dated Aug. 12, 2020, 16 pages.
Devos et al., "Practical Limits of Function Prediction", Proteins: Structure, Function and Genetics, vol. 41, pp. 98-107 (2000).
International Preliminary Report on Patentability in PCT/US2019/029817 dated Nov. 3, 2020, 14 pages.
International Preliminary Report on Patentability received for PCT application No. PCT/US2019/029795, dated Nov. 3, 2020, 7 pages.
International Preliminary Report on Patentability received for PCT application No. PCT/US2019/029798 dated Nov. 3, 2020.
International Preliminary Report on Patentability received for PCT application No. PCT/US2019/029827, dated Nov. 3, 2020, 13 pages.
Kisselev, "Polypeptide Release Factors in Prokaryotes and Eukaryotes: Same Function, Different Structure", Structure, vol. 10, pp. 8-9 (2002).
Non-Final office action received for U.S. Appl. No. 16/398,384, dated Oct. 23, 2020, 13 pages.
Whisstock et al., "Prediction of protein function from protein sequence and structure", Quarterly Reviews of BioPhysics, vol. 36, Issue 3, pp. 307-340 (2003).
Witkowski et al., "Conversion of β-Ketoacyl Synthase to a Malonyl Decarboxylase by Replacement of the Active-Site Cysteine with Glutamine", Biochemistry, vol. 38, pp. 11643-11650 (1999).
Kaddor, C., et al., "Implications of various phosphoenolpyruvate-carbohydrate phosphotransf erase system mutations on glycerol utilization and poly(3-hydroxybutyrate) accumulation in Ralstonia eutropha H16", AMB Express, 2011, vol. 1, pp. 16.
Karstens, K., et al., "Phosphotransferase protein EIIANtr interacts with SpoT, a key enzyme of the stringent response, in Ralstonia eutropha HI6", Microbiology, 2014, vol. 160, pp. 711-722.
Katalin Kovacs et al: Metabolic engineering of Cupriavidus necator H16 for the sustainable production of C3 and C5 monomers and polymers, Clnet Conference 4, Jan. 20-23, 2019 Conference paper (Abstract), 2019, p. 26.
Kazakov, A.E., et al., "Comparative genomics of regulation of fatty acid and branched-chain amino acid utilization in proteobacteria", Journal of Bacteriology, 2009, vol. 191, pp. 52-64.
Kim et al. "Effect of overexpression of Actinobacillus succinogenes phosphoenolpyruvate carboxykinase on succinate production in *Escherichia coli*" Applied and Environmental Microbiology, 2004, vol. 70, Issue 2, pp. 1238-1241.
Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.
Koller et al., "Potential and Prospects of Continuous Polyhydroxyalkanoate (PHA) Production", Bioengineering,May 29, 2015, pp. 94-121.
Koller, M., "A review on established and emerging fermentation schemes for microbial production of polyhydroxyalkanoate (PHA) biopolyesters", Fermentation,vol. 4, Apr. 23, 2018 (Apr. 23, 2018), pp. 1-30.
Koller, M., et al., "Continuous production mode as a viable process-engineering tool for efficient poly (hydroxyalkanoate) (PHA) bio-production", Chemical and Biochemical Product Engineering, vol. 28, Issue 1, 2014, pp. 65-77.
Krausse et al., "Essential role of the hprK gene inRalstonia eutropha HI6", J Mol Microbiol Biotechnol, 2009, vol. 17, pp. 146-152.
Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.
Lardi, M., et al., "σ54-Dependent Response to Nitrogen Limitation and Virulence in Burkholderia cenocepacia Strain H111" Appl. Environ. Microbiol., 2015, vol. 81, Issue 12, pp. 4077-4089.
Lee, J.N., et al., "Metabolic Engineering of Pentose Phosphate Pathway in Ralsonia eutropha for Enhanced Biosynthesis of Poly—hydroxybutyrate", Biotechnology Progress, 2003, vol. 19, Issue 5, pp. 1444-1449.
Lee, et al., "Regulation of poly—hydroxybutyrate biosynthesis by nicotinamide nucleotide in Alcaligene eutrophus" FEMS Microbiological letters, 1995, vol. 131, pp. 35-39.
Lee, et al., "Microbial Production of Ethanol from Acetate by Engineered Ralstonia Eutropha", Biotechnology and Bioprocess Engineering, vol. 21, 2016, pp. 402-407.
Leyn et al., "Control of proteobacterial centralcarbon metabolism by the HexR transcriptionalregulator: a case study in Shewanella oneidensis", Journal of Biological Chemistry, 2011, vol. 286, Issue 41, pp. 35782-35794.
Leyn, S.A., et al. "Comparative genomics and evolution of transcriptional regulons in Proteobacteria", Microbial Genomics, 2016, pp. 1-15.

(56) References Cited

OTHER PUBLICATIONS

Li, Z.J., et al., "Overexpression of NAD kinase in recombinant *Escherichia coli* harboring the phbCAB operon improves poly(3-hydroxybutyrate) production", Appl Microbial Biotechnol., 2009, vol. 83, Issue 5, pp. 939-947.

Liu, X., et al., "Comparative analysis of genes frequently regulated by drugs based on connectivity map transcriptome data" PLoS One, 2017, vol. 12, Issue 6, e0179037.

Lu, J., et al. "Studies on the production of branched-chain alcohols in engineered Ralstonia eutropha", AApplied Microbiology and Biotechnology, 2012, vol. 96, pp. 283-297.

Marc, J., et al., "Over expression of GroESL in Cupriavidus necator for heterotrophic and autotrophic isopropanol production", Metabolic Engineering,vol. 42, 2017, pp. 74-84.

March, J.C., et al., "Expression of an anaplerotic enzyme, pyruvate carboxylase, improves recombinant protein production in *Escherichia coli*" Applied and Environmental Microbiology, 2002, vol. 68, Issue 11, pp. 5620-5624.

Martin, Koller, et al., "Continuous production mode as a viable process-engineering tool for efficient poly (hydroxyalkanoate) (PHA) bio-production", Chemical And Biochemical Engineering Quarterly, vol. 28, XP002792820 ,2014, pp. 65-77.

Mckinlay, J.B., et al., "Carbon dioxide fixation as a central redox cofactor recycling mechanism in bacteria" PNAS, 2010, vol. 107, Issue 26, pp. 11669-11675.

Meng, J., et al. "High-yield anaerobic succinate production by strategically regulating multiple metabolic pathways based on stoichiometric maximumin *Escherichia coli*", Microbial Cell Factories, vol. 15, 2016, pp. 13.

Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.

Nguyen, C., et al., "Trapping the dynamic acyl carrier protein in fatty acid biosynthesis", Nature, vol. 505, No. 7483 ,Dec. 22, 2013, pp. 427-431.

Obruca, S., et al. "Application of random mutagenesis to enhance the production of polyhydroxyalkanoates by Cupriavidus necator H16 on waste frying oil". World J Microbiol Biotechnol, 2013, vol. 29, pp. 2417-2428.

Olaya-Abril et al., "Poly(3-hydroxybutyrate) hyperproduction by a global nitrogen regulator NtrB mutant strain of Paracoccus denitrificans PD1222", FEMS Microbiology Letters, 2008, vol. 365:fnx251, pp. 8.

Orita, L., et al., "Identification of mutation points in Cupriavidus necator NCIMB 11599 and genetic reconstitution of glucose-utilization ability in wild strain H16 for polyhydroxyalkanoate production" Journal of Bioscience and Bioengineering, 2012, vol. 113, Issue 1, pp. 63-69.

Papagiani, M., "Recent advances in engineering the central carbon metabolism of industrially important bacteria", Microbial Cell Factories, 2012, vol. 11, pp. 13.

Park, J-S., et al., "Metabolic Characteristics of Isocitrate Dehydrogenase Leaky Mutant of Alcaligene eutrophus and Its Utilization for Poly-Hydroxybutyrate Production" Journal of Fermentation and Bioengineering, 1996, vol. 81, Issue 3, pp. 197-205.

Park, S., et al., "Oxaloacetate and malate production in engineered *Escherichia coli* by expression of codon-optimized phosphoenolpyruvate carboxylase2 gene from Dunaliella salina", Bioprocess Biosyst Eng., 2013, vol. 36, Issue 1, pp. 127-131.

Persuhn, D.C., et al. "The transcriptional activator NtrC controls the expression and activity of glutamine synthetase in Herbaspirillum seropedicae" FEMS Microbiology Letters, 2000, vol. 192, pp. 217-221.

Pohlmann, A., et al., "Genome sequence of the bioplastic-producing "Knallgas" bacterium *Ralsonia eutropha* H16" Nature Biotechnology, 2007, vol. 24, No. 10, pp. 1257-1262.

Pryzbylski, D., et al., "Synthesis of the building block 2-hydroxyisobutyrate from fructose and butyrate by Cupriavidus necator HI6", Appl. Microbial. Biotechnol., 2013, vol. 97, 20, pp. 8875-8885.

Qi et al., "Model-driven redox pathway manipulation for improved isobutanol production in Bacillus subtilis complemented with experimental validation and metabolic profiling analysis" PLoS One, 2014, vol. 9, Issue 4, : e93815, pp. 1-11.

Raberg, M., "Ralstoni a eutropha H16 in progress: applications beside PHAs and establishment as production platform by advanced genetic tools", Critical Reviews in Biotechnology, vol. 38, Dec. 12, 2017 (Dec. 12, 2017), pp. 494-510.

Rosa, L.T., et al., "Tripartite ATP-Independent Periplasmic (TRAP) Transporters and Tripartite Tricarboxylate Transporters (TTT): From Uptake to Pathogenicity", Frontiers in Microbiology, 2018, vol. 8, pp. 16.

Sacamboio, E.N.M., et al. "The transcriptional regulator NtrC controls glucose-6-phosphate dehydrogenase expression and polyhydroxybutyrate synthesis through NADPH availability in Herbaspirillum seropedicae" Scientific Reports, 2017, vol. 7, Article No. 13546, pp. 1-12.

Sanchez, A.M., et al., "Effect of overexpression of a soluble pyridine nucleotide transhydrogenase (UdhA) on the production of poly(3-hydroxybutyrate) in *Escherichia coli*" Biotechnol Prog , 2006, vol. 22, Issue 2, pp. 420-425.

Saur, U., et al.,"The PEP-pyruvate-oxaloacetate node as the switch point for carbon flux distribution in bacteria", FEMS Microbiology Reviews, 2005, vol. 29, Issue 4, pp. 765-794.

Schlegel, H.G., et al., "Formation of the Dehydroganses for Lactate, Ethanol and Butanediol in the Strictly Aerobi Bacterium *Alcaligene eutrophus*" Microbiology, 1980, vol. 117, pp. 475-481.

Schobert, P., et al., "Unusual C3 and C4 metabolism in the chemoautotroph Alcaligenes eutrophus" Journal of Bacterialogy, 1984, vol. 159, Issue 1, pp. 167-172.

Schramke, h., et al., "Revisiting Regulation of Potassium Homeostasis in *Escherichia coli*: The Connection toPhosphate Limitation", Wiley Microbiologyopen, vol. 6, No. 3, 2017, pp. 1-16.

Schwartz, E., et al., "A proteomic view of the facultatively chemolithoautotrophic lifestyle of Ralstonia eutropha HI6" Proteomics, 2009, vol. 9, Issue 22, pp. 5132-5142.

Segura, D., et al., "Inactivation of pycA, encoding pyruvate carboxylase activity, increases polybeta-hydroxybutyrate accumulation in Azotobacter vinelandii on solid medium" Appl Microbial Biotechnol, 2004, pp. 65, Issue 4, pp. 414-418.

Sekar, B.S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate dehydrogenase ( gnd)", Biotechnology for Biofuels, 2017, vol. 10, 85, pp. 12.

Shang et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.

Shively, J.M., et al., "Something From Almost Nothing: Carbon Dioxide Fixation In Chemoautotrophs", Annu. Rev. Microbiol., vol. 52 ,1998, pp. 191-230.

Kizer L et al. Application of Functional Genomics to Pathway Optimization for Increased Isoprenoid Production. Applied andEnvironmental Microbiology. 2008. Vol. 74, No. 10 p. 3229-3241 (Year 2008).

Non-Final office action received for U.S. Appl. No. 16/398,351, dated Feb. 1, 2021, 24 pages.

Non-Final office action received for U.S. Appl. No. 16/398,401 , dated Feb. 16, 2021, 29 pages.

Non-Final office action received for U.S. Appl. No. 16/398,365, dated Jan. 25, 2021, 10 pages.

Prather KLJ et al. De nova biosynthetic pathways: Rational design of microbial chemical factories. Current Opinion in Biotechnology, 2008. 19:468-47 4 (Year: 2008).

Singh RK et al. Protein Engineering Approaches in the Post-Genomic Era. 2017. Current Protein and Peptide Science. 18, 1-11 (Year: 2017).

(56) References Cited

OTHER PUBLICATIONS

Uniprot database, entry A0A0U2WHG0, Mar. 2016.
Zhang M et al. Propagated Perturbations from a Peripheral Mutation Show Interactions Supporting WW Domain Thermostablity, 2018, Structure. 26, 1474-1485. (Year: 2018).
Cavalheiro JMBT et al. Poly(3-hydroxybutyrate) production by Cupriavidus necator using waste glycerol, Process Biochemistry, vol. 44, pp. 509-515, 2009.
Final office action received for U.S. Appl. No. 16/398,351, dated Jul. 2, 2021, 24 pages.
"Aminotransferase class III-fold pyridoxal phosphate-dependent enzyme [Aquitalea denitrificans]", NCBI Reference Sequence: WP_159877958.1, Jan. 19, 2020, 1 page.
"Aminotransferase class III-fold pyridoxal phosphate-dependent enzyme [*Aquitalea* sp. LB tupeE]", NCBI Reference Sequence: WP_178973970.1, Jul. 11, 2020, 1 page.
"Aminotransferase class III-fold pyridoxal phosphate-dependent enzyme [Chromobacterium haemolyticum]", NCBI Reference Sequence: WP_166453011.1, Apr. 6, 2020, 1 page.
"Aminotransferase class III-fold pyridoxal phosphate-dependent enzyme [Chromobacterium vaccinii]", NCBI Reference Sequence: WP_166440807.1, Apr. 6, 2020, 1 page.
"Aminotransferase class III-fold pyridoxal phosphate-dependent enzyme [Crenobacter sedimenti]", NCBI Reference Sequence: WP_163315775.1, Apr. 6, 2020, 1 page.
"Aminotransferase class III-fold pyridoxal phosphate-dependent enzyme [Neisseriaceae bacterium B2N2-7]", GenBank: MXR37125.1, Jan. 6, 2020, 2 pages.
"Aminotransferase class III-fold pyridoxal phosphate-dependent enzyme [Paludibacterium paludis]", NCBI Reference Sequence: WP_1 89532963.1, Sep. 28, 2020, 1 page.
"Aminotransferase class III-fold pyridoxal phosphate-dependent enzyme [*Paludibacterium* sp. dN 18-1]", GenBank: MTD33855.1, Nov. 24, 2019, 1 page.
"Aminotransferase class III-fold pyridoxal phosphate-dependent enzyme [Vogesella alkaliphila]", NCBI Reference Sequence: WP_189374996 1, Sep. 28, 2020, 1 page.
"Aminotransferase class III-fold pyridoxal phosphate-dependent enzyme [Vogesella fluminis]", NCBI Reference Sequence: WP_189352298 1, Sep. 28, 2020, 1 page.
"Aminotransferase class III-fold pyridoxal phosphate-dependent enzyme [Vogesella oryzae]", NCBI Reference Sequence: WP_174874069.1, Jun. 22, 2020, 1 page.
"Aspartate aminotransferase family protein [Aquitalea magnusonii]", NCBI Reference Sequence: WP_059287319.1, Dec. 31, 2020. 1 page.
"Aspartate aminotransferase family protein [Aquitalea magnusonii]", NCBI Reference Sequence: WP_089085350.1, Jul. 15, 2017, 1 page.
"Aspartate aminotransferase family protein [*Aquitalea* sp. FJL05]", NCBI Reference Sequence: WP_124643387.1, Apr. 12, 2019, 1 page.
"Aspartate aminotransferase family protein [*Aquitalea* sp. THG-DN7.12]", NCBI Reference Sequence: WP_1 37009623.1, Oct. 16, 2019, 1 page.
"Aspartate aminotransferase family protein [Chromobacterium amazonense]", NCBI Reference Sequence: WP_1 06076402.1, Mar. 16, 2018, 1 page.
"Aspartate aminotransferase family protein [Chromobacterium haemolyticum]", GenBank: OQS32233.1, Apr. 6, 2017, 2 pages.
"Aspartate aminotransferase family protein [Chromobacterium haemolyticum]", GenBank: OQS37730.1, Apr. 6, 2017, 2 pages.
"Aspartate aminotransferase family protein [Chromobacterium haemolyticum]", NCBI Reference Sequence: WP_043593957.1, Apr. 15, 2016, 1 page.
"Aspartate aminotransferase family protein [Chromobacterium haemolyticum]", NCBI Reference Sequence: WP_081556739.1, Apr. 8, 2017, 1 page.
"Aspartate aminotransferase family protein [Chromobacterium haemolyticum]", NCBI Reference Sequence: WP_081576047.1, Apr. 8, 2017, 1 page.
"Aspartate aminotransferase family protein [Chromobacterium haemolyticum]", NCBI Reference Sequence: WP_161523523.1, Oct. 5, 2020, 1 page.
"Aspartate aminotransferase family protein [Chromobacterium paludis]", NCBI Reference Sequence: WP_1 49295777.1, Oct. 5, 2020, 1 page.
"Aspartate aminotransferase family protein [Chromobacterium phragmitis]", NCBI Reference Sequence: WP_114062556.1, Dec. 20, 2020.
"Aspartate aminotransferase family protein [*Chromobacterium* sp. ATCC 53434]", NCBI Reference Sequence: WP_101708025.1, Jan. 10, 2018.
"Aspartate aminotransferase family protein [*Chromobacterium* sp. LK11]", NCBI Reference Sequence: WP_048412320.1, Apr. 15, 2016, 1 page.
"Aspartate aminotransferase family protein [*Chromobacterium* sp. LK1]", NCBI Reference Sequence: WP_048411976.1, Apr. 15, 2016, 1 page.
"Aspartate aminotransferase family protein [*Chromobacterium* sp. MWU13-2610]", NCBI Reference Sequence: WP_103321487.1, Jan. 31, 2018, 1 page.
"Aspartate aminotransferase family protein [*Chromobacterium* sp. MWU14-2602]", NCBI Reference Sequence: WP_103903523.1, Feb. 10, 2018, 1 page.
"Aspartate aminotransferase family protein [*Chromobacterium* sp. Panama]", NCBI Reference Sequence: WP_107799474.1, Apr. 25, 2018, 1 page.
"Aspartate aminotransferase family protein [Chromobacterium sphagni]", NCBI Reference Sequence: WP_071116856.1, Aug. 23, 2017, 1 page.
"Aspartate aminotransferase family protein [Chromobacterium subtsugae]", NCBI Reference Sequence: WP_047237256.1, Mar. 20, 2018, 1 page.
"Aspartate aminotransferase family protein [Chromobacterium subtsugae]", NCBI Reference Sequence: WP_047243213.1, Apr. 15, 2016, 1 page.
"Aspartate aminotransferase family protein [Chromobacterium subtsugae]", NCBI Reference Sequence: WP_047257673.1, Apr. 15, 2016, 1 page.
"Aspartate aminotransferase family protein [Chromobacterium vaccinii]", NCBI Reference Sequence: WP_046156378.1, Oct. 25, 2019, 1 page.
"Aspartate aminotransferase family protein [Chromobacterium vaccinii]", NCBI Reference Sequence: WP_104946997.1, Mar. 4, 2018, 1 page.
"Aspartate aminotransferase family protein [Chromobacterium violaceum]", NCBI Reference Sequence: WP_011135573.1, Jul. 28, 2019, 1 page.
"Aspartate aminotransferase family protein [Chromobacterium violaceum]", NCBI Reference Sequence: WP_048405256.1, Apr. 15, 2016, 1 page.
"Aspartate aminotransferase family protein [Chromobacterium violaceum]", NCBI Reference Sequence: WP_081573061.1, Apr. 8, 2017, 1 page.
"Aspartate aminotransferase family protein [Chromobacterium violaceum]", NCBI Reference Sequence: WP_152637556.1, Oct. 31, 2019, 1 page.
"Aspartate aminotransferase family protein [*Crenobacter* sp. GY 70310]", NCBI Reference Sequence: WP_136552942.1, Oct. 16, 2019, 1 page.
"Aspartate aminotransferase family protein [Gulbenkiania indica]", NCBI Reference Sequence: WP_055434103.1, May 14, 2017, 1 page.
"Aspartate aminotransferase family protein [Gulbenkiania mobilis]", NCBI Reference Sequence: WP_054286466.1, May 14, 2017, 1 page.
"Aspartate aminotransferase family protein [Paludibacterium purpuratum]", NCBI Reference Sequence: WP_1 33682408.1, May 12, 2019, 1 page.

(56) References Cited

OTHER PUBLICATIONS

"Aspartate aminotransferase family protein [Paludibacterium yongneupense]", NCBI Reference Sequence: WP_028535161.1, Apr. 15, 2016, 2 pages.
"Aspartate aminotransferase family protein [Pseudogulbenkiania ferrooxidans]", NCBI Reference Sequence: WP_008952788.1, Apr. 15, 2016, 2 pages.
"Aspartate aminotransferase family protein [Pseudogulbenkiania ferrooxidans]", NCBI Reference Sequence: WP_021478068.1, Apr. 15, 2016, 1 page.
"Aspartate aminotransferase family protein [*Pseudogulbenkiania* sp. MAI-1]", Ncbi Reference Sequence: WP_024302818.1, Apr. 15, 2016, 2 pages.
"Aspartate aminotransferase family protein [*Pseudogulbenkiania* sp. NH8B]", Ncbi Reference Sequence: WP_014087389.1, Apr. 15, 2016, 2 pages.
"Aspartate aminotransferase family protein [Pseudogulbenkiania subflava]", NCBI Reference Sequence: WP_085275708.1, Apr. 22, 2017, 1 page.
"Aspartate aminotransferase family protein [Vogesella indigofera]",NCBI Reference Sequence: WP_120809711.1, Nov. 4, 2018, 1 page.
"Aspartate aminotransferase family protein [Vogesella mureinivorans]", NCBI Reference Sequence: WP_147694092.1, Oct. 5, 2020, 1 page.
"Aspartate aminotransferase family protein [Vogesella perlucida]", NCBI Reference Sequence: WP_147687830.1, Oct. 5, 2020, 1 page.
"Aspartate aminotransferase family protein [*Vogesella* sp. Eb]", NCBI Reference Sequence: WP_047966302.1, Apr. 15, 2016, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [Vogesella urethralis]", NCBI Reference Sequence: WP_144371715.1, Oct. 5, 2020, 1 page.
"Aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB:5S4G_A, Dec. 1, 2020, 2 pages.
"Multispecies: aspartate aminotransferase family protein [Aquitalea]", NCBI Reference Sequence: WP_045848621.1, Apr. 15, 2016, 1 page.
"Multispecies: aspartate aminotransferase family protein [Aquitalea]", NCBI Reference Sequence: WP_103523625.1, Aug. 6, 2020, 1 page.
"Multispecies: aspartate aminotransferase family protein [Chromobacterium]", NCBI Reference Sequence: WP_019104435.1, Apr. 18, 2017, 1 page.
"Multispecies: aspartate aminotransferase family protein [Chromobacterium]", NCBI Reference Sequence: WP_043572477.1, Apr. 15, 2016, 1 page.
"Multispecies: aspartate aminotransferase family protein [Chromobacterium]", NCBI Reference Sequence: WP_043629242.1, Oct. 31, 2016, 1 page.
"Multispecies: aspartate aminotransferase family protein [Chromobacterium]", WP_043638691.1, Nov. 11, 2020, 1 page.
"Multispecies: aspartate aminotransferase family protein [Microvirgula]", NCBI Reference Sequence: WP_028498438.1, Jul. 14, 2018, 1 page.
U.S. Appl. No. 16/372,072, Corrected Notice of Allowability dated Jan. 26, 2021, 2 pages.
U.S. Appl. No. 16/372,072, Notice of Allowance dated Jul. 17, 2020, 11 pages.
U.S. Appl. No. 16/372,072, Notice of Allowance dated Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement dated Dec. 11, 2019, 7 pages.
U.S. Appl. No. 16/372,072, Response filed Jun. 8, 2020 to Non Final Office Action dated Mar. 6, 2020, 11 pages.
U.S. Appl. No. 16/372,072, Restriction Requirement dated Dec. 11, 2019, 9 pages.
U.S. Appl. No. 16/372,083, Notice of Allowability dated Sep. 22, 2021, 5 pages.
U.S. Appl. No. 16/372,083, Notice of Allowance dated Aug. 31, 2021, 9 pages.
U.S. Appl. No. 16/372,083, Preliminary Amendment filed Jul. 30, 2019, 4 pages.
U.S. Appl. No. 16/372,083, Response filed Apr. 12, 2021 to Restriction Requirement dated Mar. 8, 2021, 8 pages.
U.S. Appl. No. 16/372,083, Response filed Jul. 27, 2021 to Non Final Office Action dated Apr. 27, 2021, 11 pages.
U.S. Appl. No. 16/372,083, Response filed Dec. 18, 2020 to Restriction Requirement dated Oct. 19, 2020, 7 pages.
U.S. Appl. No. 16/372,083, Restriction Requirement dated Mar. 8, 2021, 6 pages.
U.S. Appl. No. 16/372,083, Restriction Requirement dated Oct. 19, 2020, 8 pages.
U.S. Appl. No. 16/372,083, Supplemental Amendment filed for Non-Final Office Action dated Apr. 27, 2021, 8 pages.
U.S. Appl. No. 16/372,092, Non Final Office Action dated Mar. 4, 2021, 9 pages.
U.S. Appl. No. 16/372,092, Response filed Jun. 2, 2021 to Non Final Office Action dated Mar. 4, 2021, 11 pgs.
U.S. Appl. No. 16/372,092, Response filed Sep. 21, 2021 to Final Office Action dated Jul. 26, 2021, 11 pages.
U.S. Appl. No. 16/372,092, Response filed Dec. 17, 2020 to Restriction Requirement dated Oct. 21, 2020, 6 pages.
U.S. Appl. No. 16/372,092, Restriction Requirement dated Oct. 21, 2020, 7 pages.
U.S. Appl. No. 16/372,099, Non Final Office Action dated Jul. 9, 2021, 14 pages.
U.S. Appl. No. 16/372,099, Response filed May 18, 2021 to Restriction Requirement dated Mar. 19, 2021, 6 pages.
U.S. Appl. No. 16/372,099, Restriction Requirement dated Mar. 19, 2021, 6 pages.
U.S. Appl. No. 16/372,106, Non Final Office Action dated Apr. 30, 2021, 26 pages.
U.S. Appl. No. 16/372,106, Response filed Jan. 19, 2021 to Restriction Requirement dated Dec. 28, 2020, 8 pages.
U.S. Appl. No. 16/372,106, Response filed Jun. 15, 2021 to Non Final Office Action dated Apr. 30, 2021, 12 pages.
U.S. Appl. No. 16/372,106, Restriction Requirement dated Dec. 28, 2020, 7 pages.
U.S. Appl. No. 16/399,145, Advisory Action dated Feb. 1, 2021, 4 pages.
U.S. Appl. No. 16/399,145, Final Office Action dated Dec. 4, 2020, 17 pages.
U.S. Appl. No. 16/399,145, Non Final Office Action dated Jun. 17, 2021, 20 pages.
U.S. Appl. No. 16/399,145, Response filed Jan. 25, 2021 to Final Office Action dated Dec. 4, 2020, 12 pages.
U.S. Appl. No. 16/399,145, Response filed Jun. 3, 2020 to Restriction Requirement dated Apr. 17, 2020, 7 pages.
U.S. Appl. No. 16/399,145, Response filed Sep. 15, 2021 to Non Final Office Action dated Jun. 17, 2021, 11 Pages.
U.S. Appl. No. 16/399,145, Response filed Nov. 6, 2020 to Non Final Office Action dated Aug. 12, 2020, 12 pages.
U.S. Appl. No. 16/399,145, Restriction Requirement dated Apr. 17, 2020, 9 pages.
Brigham, C.J., et al., "Engineering Ralstonia eutropha for Production of Isobutanol from C02, H2 and 02", Advanced Biofuels and Bioproducts, (2013) Chapter 39, pp. 1065-1090.
"Cupriavidus necator", Wikipedia, Retrieved from Internet URL: https://en.wikipedia.org/wiki/Cupriavidus_necator#:-:text= Cupriavidus%20necator"/o20is%20a%20hydrogen,a%20source% 20of"/o20energy%20C., Feb. 25, 2021, 07 Pages.

(56) References Cited

OTHER PUBLICATIONS

Devereaux, J., et al., "A comprehensive set of sequence analysis programs for the VAX", Nucleic Acids Research, vol. 12, Issue 1, Part 1, Jan. 11, 1984, pp. 387-395.
Final Office Action received for U.S. Appl. No. 16/372,092, dated Jul. 26, 2021, 10 Pages.
GenBank QOK7M4.2006. GenBank. p. 1 (Year: 2006).
GenBank Q0KC80.2006. GenBank. p. 1 (Year: 2006).
GenBank Q2Z1A9. 2006. GenBank. p. 1 (Year: 2006).
GenBank Q0K5F4. 2006. GenBank. p. 1 (Year: 2006).
Hensirisak et al. "Scale-Up of Microbubble Dispersion Generator for Aerobic Fermentation", Applied Biochemistry and Biotechnology vol. 101, 2002, p. 211-227 (Year: 2002).
https://www.clrblu.com/aeration/, "Aeration" (Year: 2021).
International Application Serial No. PCT/US2019/025189, International Preliminary Report on Patentability dated Oct. 15, 2020, 9 pages.
International Application Serial No. PCT/US2019/025194, International Preliminary Report on Patentability dated Oct. 15, 2020, 15 pages.
International Application Serial No. PCT/US2019/025194, Invitation to Pay Additional Fees dated Jul. 1, 2019, 14 pages.
International Application Serial No. PCT/US2019/025202, International Preliminary Report on Patentability dated Oct. 15, 2020, 12 pages.
International Application Serial No. PCT/US2019/025218, Invitation to Pay Additional Fees dated Jun. 25, 2019, 09 pages.
International Application Serial No. PCT/US2019/029956, International Preliminary Report on Patentability dated Nov. 12, 2020, 12 pages.
International Application Serial No. PCT/US2019/029973, International Preliminary Report on Patentability dated Nov. 12, 2020, 12 pages.
International Preliminary Report on Patentability for PCT application No. PCT/US2019/025211, dated Oct. 15, 2020, 13 pages.
Shii et al., Uniprot database, accession No. G2J4X6, Nov. 2011, pp. 2.
Ishizaki, A., et al., "Microbial production of poly-D-3-hydroxybutyrate from C02", Applied Microbiology and Biotechnology, vol. 57, Oct. 2001, pp. 6-12.
Ishizuka, H., et al., "Putrescine Oxidase of Micrococcus Rubens: Primary Structure and *Escherichia coli*", Journal of General Microbiology, vol. 139, 1993, pp. 425-432.
Jones, G.W. and Kennedy, Re., "Prevention of Gas Explosions by Controlling Oxygen Concentration", Industrial and Engineering Chemistry, vol. 27, Issue 11, 1935, pp. 1344-1346.
Judger, B-E., et al., "An analysis of the changes in soluble hydrogenase and global gene expression in Cupriavidusnecator (Ralstonia eutropha) HI6 grown in heterotrophic diauxic batch culture", Microbial Cell Factories, vol. 14, 2015, pp. 1-11.
Kaster et al., "Increased Oxygen Transfer in a Yeast Fermentation Using a Microbubble Dispersion", Applied Biochemistry and Biotechnology vol. 24/25, 1990, p. 469-484 (Year: 1990).
Lasson, K.T., et al.,"Bioreactor design for synthesis gas fermentations", Fuel, vol. 70, Issue 5,1991, pp. 605-614.
Kyte, J., et al., "A simple method for displaying the hydropathic character of a protein", Journal of Molecular Biology, vol. 157, No. 1, May 5, 1982, pp. 105-132.
Lin, S., et al., "Biotin Synthesis Beings by Hijacking the Fatty Acid Synthesis Pathway," Nature Chemical Biology, vol. 6, No. 9, Sep. 2010, pp. 682-688.
Nui, M., et al., Metabolic Engineering of Corynebacterium glutamicum for Fuel Ethanol Production under Oxygen Deprivation Conditions. 2004. J Mol. Microbiol. Biotechnol., vol. 8, pp. 243-254.
Lu, et al., "Studies in the production of branched-chain alcohols in engineered Ralstonia eutropha", Bioenergy and Biofuels, 96, 2012, 283-297.
Lucas et al., GenBank accession No. ACU95033, Aug. 26, 2009, p. 1.
Maddipati, P., "Ethanol production from syngas by Clostridium strain P11 using corn steep liquor as a nutrient replacement to yeast extract", Bioresoure Technology, vol. 102, Issue 11, 2011, pp. 6494-6501.
Myers, Eugene, et al., "Optimal alignments in linear space", Computer Applications in the Biosciences, vol. 4, 1988, pp. 11-17.
Needleman, S.B., et al., "A general method applicable to the search for similarities in the amino acid sequence of two proteins". Journal of Molecular Biology, vol. 48, Issue 3, Mar. 1970, pp. 443-453.
NETL brochure, "Syngas composition", accessed online on (www.netl.doe.gov/research/coal/energy systems/gasification/gasifipedia/syngas-composition), Jul. 3, 2021, total pp. 1-2 (Year: 2021).
Non Final Office Action received for U.S. Appl. No. 16/372,072, dated Mar. 6, 2020, 20 Pages.
Non Final Office Action received for U.S. Appl. No. 16/372,083, dated Apr. 27, 2021, 14 Pages.
Pearson, W.R., et al., "Improved tools for biological sequence comparison", Proceedings of the National Academy of Science of the United States of America, vol. 85, Issue 8, Apr. 1988, pp. 2444-2448.
Phillips, J.R, et al., "Syngas Fermentation: A Microbial Conversion Process of Gaseous Substrates to Various Products", Fermentation, vol. 3, Issue 2, 2017, pp. 26.
Sadowski et al. "The sequence-structure relationship and protein function prediction", Current Opinion in Structural Biology, 19 pp. 357-362, 2009.
Seffernick et al.,"Melelamine Deaminase and Atrazine Chlorohydrolase: 98 Percent Identical but Functionally Different", Journal of Bacteriology, 183(8), pp. 2405-2410, 2001.
Shulman, A.I., et al. "Structural determinants of allosteric ligand activation in RXR heterodimers," Cell, vol. 116, Issue 3, Feb. 6, 2004, pp. 417-429.
Slabu et al., "Discovery, Engineering and Synthetic Application of Transaminase Biocatalysts," ACS Catalysis 7, 2017, pp. 8263-8284.
Smith, T.F., et al., "Comparison of biosequences", Advances in Applied Mathematics, vol. 2, Issue 4, Dec. 1981, pp. 182-189.
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue4, 1994, pp. 425-427.
Tang et al.,"Identification of Dehalobacter reductive dehalogenases that catalyse dechlorination of chloroform, 1, 1,1-trichloroethane and 1,1-dichloroethane", Phil Trans Royal Society Publishing, 368:20120318, pp. 1-10, 2013.
"TPA: aspartate aminotransferase family protein [*Betaproteobacteria bacterium*]", GenBank: HEL32111.1, Mar. 2, 2020, 1 page.
Final office action received for U.S. Appl. No. 16/398,351, dated Feb. 28, 2022, 11 pages.
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Non-Final office action received for U.S. Appl. No. 16/372,106, dated Apr. 5, 2022, 33 pages.
Advisory Action received for U.S. Appl. No. 16/372,092, dated Oct. 7, 2021, 3 pages.
Advisory Action received for U.S. Appl. No. 16/372,099, dated Feb. 22, 2022, 3 pages.
Advisory Action received for U.S. Appl. No. 16/372,106, dated Mar. 9, 2022, 3 pages.
Advisory Action received for U.S. Appl. No. 16/399,145, dated Mar. 4, 2022, 4 pages.
aspartate aminotransferase family protein [Rhodobacteraceae bacterium CH30], GenBank: RQW28969 1, Dec. 2, 2018, 2 pages.
Baltz et al. "Manual of Industrial Microbiology and Biotechnology", ASM Press, 2010, 4 Pages (Abstract).
Berg " Biochemistry 5th ed.", W H Freeman and Company, 2002, 1 Page (Abstract).
Database UniProt, "RecName: Full=Thiopurine S-methyltransferase [ECO:0000256|HAMAPRule:MF_00812,

(56) References Cited

OTHER PUBLICATIONS

ECO:0000256|SAAS:SAAS00896910}; EC=2.1.1.67; AltName: Full= Thiopurine methyltransferase ", EBI accession No. UNIPROT:A0A1 L8MA47 Database accession No. A0A1L8MA47, Mar. 15, 2017, 04 Pages.
Database UniProt, "SubName: Full=Acyl-ACP thioesterase ", retrieved from EBI accession No. EBI accession No. UNIPROT:R7CHF5 Database accession No. R7CHF5, Jul. 24, 2013, 03 Pages.
Database UniProt, "RecName: Full=Thiopurine S-methyltransferase [ECG:0000256|HAMAPRule:MF_00812, zCO:0000256|SAAS:SAAS00896910}; EC=2.1.1.67; AltName: Full= Thiopurine methyltransferase " ,EBI accession No. UNIPROT:A0A009ZVV4 Database accession No. A0A009ZVV4, Jun. 11, 2014, 04 Pages.
Final Rejection received for U.S. Appl. No. 16/372,099, dated Dec. 21, 2021, 17 pages.
Final Rejection received for U.S. Appl. No. 16/372,106, dated Dec. 22, 2021, 32 pages.
Final Rejection received for U.S. Appl. No. 16/372,106, dated Oct. 4, 2021, 29 pages.
Final Rejection received for U.S. Appl. No. 16/399,145, dated Dec. 22, 2021, 20 pages.
Folsom, J.P. et al., "Physiological and Proteomic Analysis of *Escherichia coli* Iron-Limited Chemostat Growth," Journal of Bacteriology, vol. 196, No. 15, pp. 2748-2761, Aug. 2014.
Harder et al., "Physiological responses to nutrient limitation", Annual Review of Microbiology, vol. 37, 1983, pp. 1-23.
Huang et al., "Bacterial and Yeast Cultures - Process Characteristics, Products, and Applications", Bioprocessing for Value-Added Products from Renewable Resources, pp. 185-223, Dec. 2007 (Year: 2007).
Kihlberg," The Microbe as a Source of Food" Annual Review of Microbiology, vol. 26, 1972, pp. 427-466.
Manandhar, M., et al., "Pimelic acid, the first precursor of the Bacillus subtilis biotin synthesis pathway, exists as the free acid and is assembled by fatty acid synthesis: Bacillus subtilis biotin synthesis", Molecular Microbiology, vol. 104, No. 4, Mar. 3, 2017, pp. 595-607.
Non Final Action received for U.S. Appl. No. 16/398,351, dated Jul. 5, 2022, 12 Pages.
Non Final Action received for U.S. Appl. No. 16/398,401, dated Sep. 1, 2022, 32 pages.
Non-Final office action received for U.S. Appl. No. 16/398,401, dated Nov. 9, 2021, 38 pages.
Non-Final rejection received for U.S. Appl. No. 16/372,106, dated Apr. 5, 2022, 33 pages.
Non-Final Rejection received for U.S. Appl. No. 16/372,092, dated Nov. 26, 2021, 10 Pages.
Notice of Allowance received for U.S. Appl. No. 16/372,099, dated Apr. 15, 2022, 11 pages.
Ogawa et al.," Role of Phosphoenolpyruvate in the NADP-lsocitrate Dehydrogenase and Isocitrate Lyase Reaction in *Escherichiacoli*", Journal of Bacteriology, vol. 189, No. 3, Feb. 2007, pp. 1176-1178.
Response to Final Office Action for U.S. Appl. No. 16/372,099, filed Feb. 8, 2022, 9 pages.
Response to Final Office Action received for U.S. Appl. No. 16/399,145, filed Feb. 22, 2022, 10 pages.
Response to Final Rejection for U.S. Appl. No. 16/372,106, filed Dec. 9, 2021, 9 pages.
Response to Final Rejection for U.S. Appl. No. 16/372,106, filed Feb. 16, 2022, 9 pages.
Response to Non Final Office Action for U.S. Appl. No. 16/372,099, filed Oct. 7, 2021, 8 pages.
Response to Non-Final Rejection for U.S. Appl. No. 16/372,092, filed Feb. 28, 2022, 9 pages.
Stanbury et al. "Principles of Fermentation Technology", 3rd Edition, Aug. 31, 2016, 4 Pages.(Abstract).
Non Final Rejection received for U.S. Appl. No. 16/372,092, dated Sep. 15, 2022, 11 Pages.
Ghosalkar et al., "Oxygen Uptake Rate Measurement by Modified Dynamic Method and Effect of Mass-Transfer Rates on Growth of Pichia Stipitis: Modeling and Experimental Data Comparison", Austin Journal of Biotechnology Bioengineering, vol. 3, Issue 3, 06 p. 2016.
Kirk et al., "Quantification of the oxygen uptake rate in a dissolved oxygen controlled oscillating jet-driven microbioreactor", Journal of Chemical Technology, vol. 91, pp. 823-831, 2015.
Final office action received for U.S. Appl. No. 16/398,401, dated Feb. 6, 2023, 25 pages.
GenBank A6VKV4 GenBank 2012 pp. 1-4.
GenBank Q0K790, GenBank, 2006; p. 1.
GenBank Q46WX6, GenBank, 2006; pp. 1-2.
GenBank Q474V2, GenBank, 2006; pp. 1-2.
GenBank QOK4C1, GenBank, 2006; p. 1.

\* cited by examiner

MATERIALS AND METHODS FOR CONTROLLING PHA BIOSYNTHESIS IN PHA-GENERATING SPECIES OF THE GENERA *RALSTONIA* OR *CUPRIAVIDUS* AND ORGANISMS RELATED THERETO

PRIORITY CLAIM

The present application claims the benefit of U.S. Provisional Patent Application No. 62/665,751 filed May 2, 2018, which is incorporated by reference herein for all purposes.

FIELD

The present disclosure relates generally to increasing the yield of a biomass having a reduced level of polyhydroxyalkanoate within a desired target range. In particular, the present disclosure relates to the aerobic continuous culturing of the organism under one or more specific limitation conditions and/or stress response conditions.

BACKGROUND

Organisms have a limited ability to control their environment and therefore may respond to environmental conditions by changing themselves. Such changes have been reported to include genotypic changes, wherein the microorganism may express certain sets of genes to be functionally and structurally adjusted to a set of conditions, or phenotypic responses of a given genotype to environmental changes, which confers a high level of versatility. In industrial bioprocesses, growth can be manipulated by limiting the availability of certain nutrients, or by depriving specific nutrients altogether, to force a productive microbial physiological state (Harder, W., & Dijkhuizen, L. Annual Review of Microbiology 1983 37(1):1-23). This is because under conditions of nutrient limitation a phenomenon known as overflow metabolism (also known as energy spilling uncoupling or spillage) occurs in many bacteria (Russell, J. B. Journal of Molecular Microbiology and Biotechnology 2007 13:1-11). In growth conditions in which there is a relative excess of a carbon source but other nutrients (e.g. phosphorous, nitrogen and/or oxygen) are limiting cell growth, overflow metabolism results in the utilization of such excess energy (or carbon), not for biomass formation but for the excretion of metabolites, typically organic acids.

In *Cupriavidus necator* (*C. necator*), previously known as *Ralstonia eutropha*, a modified form of overflow metabolism occurs in which excess carbon is sunk into the intracellular storage carbohydrate polyhydroxybutyrate (PHB). PHB falls within the broader class of polyhydroxyalkanoates (PHAs), which are key intracellular carbon and energy storage compounds enabling a large number of prokaryotic cell types to survive periods of starvation and other stressful conditions. Due in part to their thermoplastic properties and biodegradability, PHAs have found various applications in areas such as the chemical industry and medicine. As a result, a significant amount of research has focused on maximizing PHA production in batch or fed-batch fermentations of *C. necator* for use in several products.

For example, single cell protein, namely edible unicellular organisms intended to be used as food or feedstocks, has been increasingly considered as an attractive biotechnology product within the last few decades. See, for example, Kihlberg, R. Annual Review of Microbiology, 1972, 26:427-466; and U.S. Pat. No. 6,207,217. In particular, single cell protein made from polyhydroxyalkanoate-producing microorganisms such as *C. necator* has been recently explored as a component of animal feed (Egers, J. and Steinbuchel, A. Applied Environmental Microbiology 2014 80(24):7702-7709; and Raberg et al. PLOS ONE 2014 9(5):e95907). Polyhydroxyalkanoates naturally accumulate in *C. necator* and similar organisms and serve as intracellular storage compounds for carbon and energy.

However, such organisms have not been fully exploited as a feed because the most frequently contained polyhydroxyalkanoate polymer within the cells is poly(3-hydroxybutyrate) which is rarely digestible and offers reduced nutritional value. The polyhydroxybutyrate component also decreases the protein content of the organism. In addition, polyhydroxybutyrate storage compound in the cytoplasm of the organism takes up physical space, leaving less available for more nutritive compounds. Furthermore, in some instances, the polyhydroxybutyrate components have been shown to have a detrimental impact on biological functions, such as digestive system processes.

In recent work by Boon (U.S. Pat. No. 8,603,518) and Nonato (International Patent Application Publication No. WO 2015/149147), it was shown that adding polyhydroxybutyrate depolymerase enzymes to a feed mixture can result in an increase in the digestibility of the polyhydroxybutyrate. However, the total protein content for these feed mixtures is still reduced. Kunasundari et al. (PLOS ONE 2013 8(10):e78528) discloses a biological recovery process of polyhydroxyalkanoate which forms the basis for a combined synergetic feed and purification and separation process of polyhydroxyalkanoate granules from lyophilized cells of *C. necator* H16.

Even in view of these technologies, the need remains for improved methods of producing high yields of microorganism biomass that contains a low level of polyhydroxyalkanoates within a desired concentration range. The following disclosure addresses this and other needs.

SUMMARY

The present disclosure generally relates to methods for producing cellular biomass in continuous fermentation systems, wherein the biomass has a reduced polyhydroxyalkanoate level that is within a desired concentration range. When the biomass generated using the method is employed for example as a component of an animal feed, the biomass provides increased nutritional value and reduced digestive distress. For example, it is beneficial for *Cupriavidus* or *Ralstonia* used as an animal feed product to have a lower level of polyhydroxyalkanoate production than that of wild type strains. It is also desirable, however, for the organism to produce enough polyhydroxyalkanoate to provide a related nutritional benefit to the feed composition. In addition, is advantageous for the fermentation processes used to generate the biomass to be able to balance high cell growth with adequate polyhydroxyalkanoate production in a continuous process. The inventors have now surprisingly discovered particular methods that overcome the difficulties of using conventional fermentation processes to simultaneously meet these competing demands, In one aspect, the disclosure is to a method for producing a biomass in a fermentation system. The method includes providing an organism belonging to a genus selected from the group consisting of *Cupriavidus* and *Ralstonia*. The method further includes culturing a population of the organism in the fermentation system. The method further includes independently controlling the concentration of each of one or more selected limiting nutrients in at least one reactor of the fermentation system. The selected limiting nutrients include nitrogen, phosphorous, or a combination thereof. The method further includes operating the fermentation system under continuous fermentation conditions comprising a nitrogen concentration between 1 mM and 5 mM in at least one reactor of the fermentation system and/or a phosphorous concentration between 0.2 mM and 1 mM in the at least one reactor. The method further includes maintaining a population biomass production rate of at least 0.5 g/L/h in the at least one reactor. The population biomass includes between 5 wt % and 25 wt % polyhydroxyalkanoate In another aspect the disclosure is to a biomass product. The biomass is produced using the method disclosed herein.

In another aspect, the disclosure is to an animal feed composition. The animal feed includes the biomass disclosed herein.

DETAILED DESCRIPTION

The present disclosure provides materials, methods, and strategies related to particular nutrient limitation conditions for organisms, thereby improving carbon uptake and conversion to cellular biomass. In one non-limiting embodiment, the method includes providing an organism belonging to a genus selected from the group consisting of *Cupriavidus* and *Ralstonia*, or an organism with similar properties thereto. In certain aspects, the organism is a *Cupriavidus necator, Cupriavidus metallidurans, Cupriavidus taiwanensis, Cupriavidus pinatubonensis, Cupriavidus basilensis*, or *Ralstonia pickettii*, or an organism with similar properties thereto. In some embodiments, the organism is *Cupriavidus necator* or an organism with properties similar thereto.

*Cupriavidus necator* (also referred to as *Hydrogenomonas eutrophus, Alcaligenes eutropha, Ralstonia eutropha,* and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *Cupriavidus necator* include microaerophilicity, copper resistance (Makar and Casida; 1987), bacterial predation (Byrd et al., 1985; Sillman & Casida, 1986; Zeph & Casida, 1986) and polyhydroxybutyrate (PHB) synthesis. In addition, the cells have been reported to be capable of both aerobic and nitrate dependent anaerobic growth (Makar and Casida; 1987). A non-limiting example of a *Cupriavidus necator* organism useful in the present invention is a *Cupriavidus necator* of the H16 strain. In one non-limiting embodiment, a *Cupriavidus necator* host of the H16 strain with at least a portion of the phaCAB gene locus knocked out is used. Reference to an organism with properties similar to those of the groups and species disclosed herein, indicates that the organism has one or more of the aforementioned properties of *Cupriavidus necator*.

In one non-limiting embodiment, the method further includes culturing a population of the provided organism in a fermentation system. The cultured population can be a substantially pure culture of the provided organism. As used herein, the phrase "substantially pure culture" refers to a culture or population of the organism in which less than 20%, e.g., less than 15%, less than 10%, less than 5%, less than 2%, less than 1%, less than 0.5%, less than 0.25%, less than 0.1%, less than 0.01%, less than 0.001%, or less than 0.0001% of the total number of viable cells in the culture are viable cells other than the altered microorganism, e.g., other bacterial, fungal (including yeast), mycoplasmal, or protozoan cells. The culture of the organism population includes the cells and a growth, storage, or transport medium. Media can be liquid, semi-solid (e.g., gelatinous media), or frozen.

Non-limiting examples of fermentation systems suitable for use with the methods disclosed herein include a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced circulation, a bubble column fermenter, a fixed (packed)-bed column fermenter, a single horizontal fermenter having multiple compartments, and a multistage column fermenter. Each individual fermenter or autoclave of the fermentation system can be referred to herein as a reactor or bioreactor of the fermentation system. In some embodiments, the fermentation system includes a single stage continuous stirred tank reactor. In certain aspects, the only reactor in the fermentation system is a single stage continuous stirred tank reactor.

In some embodiments, the method further includes independently controlling the concentration of each of one or more selected limiting nutrients in at least one reactor of the fermentation system. The number of limiting nutrients having their concentrations controlled can be, for example, one, two, three, four, five, six, seven, eight, nine, ten, or more than ten. In certain aspects, the concentration of each of the one or more selected limiting nutrients is controlled in each reactor of the fermentation system. In some embodiments, the limiting nutrients include nitrogen, phosphorous, iron, sulphate, potassium, and oxygen. In certain aspects, the one or more selected limiting nutrients include nitrogen. In certain aspects, the one or more limiting nutrients include phosphorous.

Non-limiting examples of specific limitation conditions under which the organisms of the present invention can be cultured include iron limitations, sulphate limitations, nitrogen limitations, potassium limitations, oxygen limitations, phosphorus limitations, carbon limitations, and gradients and combinations thereof. For example, specific iron and/or sulphate limitation can impact the synthesis of iron-sulphur proteins and cytochromes and can manipulate the electron transport chains of the organism. This specific limitation condition can be used alone or in combination with nitrogen and/or phosphorus limitation to increase the production of, for example and without limitation, organic acids including, but not limited to, lactic acid, acetic acid, formic acid, and pyruvic acid. The specific limitation condition of a potassium gradient can be used to generate products of oxidative metabolism. This specific limitation condition can be used alone or in combination with nitrogen and/or phosphorus limitation to increase the synthesis of organic acids including, but not limited to, lactic acid, acetic acid, formic acid and pyruvic acid. The specific limitation condition of oxygen limitation can be utilized to disrupt the redox balance of the organism. Oxygen limitation can be used alone or in combination with nitrogen and/or phosphorus limitation, iron and/or sulphur limitation, and/or potassium limitation to increase the synthesis of organic acids including, but not limited to, lactic acid, acetic acid, formic acid and pyruvic acid. In some embodiments, the nutrient limitation conditions include a nitrogen limitation condition, a phosphorous limitation condition, and an oxygen limitation condition.

In addition, the specific limitation condition of carbon limitation with concurrent carbon feedstock utilization can be used to achieve increased carbon uptake in the organism. In one non-limiting embodiment, a carbon source is continually supplied at a rate equal to, or within, 5% of product formation for carbon limitation. Carbon limitation can be used alone or in combination with oxygen and/or nitrogen and/or phosphorus and/or iron and/or sulphur and/or potassium limitation.

Stress conditions can also be used to activate inducible promoters responsive to these conditions. Non-limiting examples of stress response conditions include physical environmental conditions that can be imposed on the organism such as temperature and pressure.

For embodiments in which nitrogen is selected as a limiting nutrient, the limiting concentration of the nitrogen can be, for example, 8.5 mM, 6.5 mM, 5 mM, 3.8 mM, 2.9 mM, 2.3 mM, 1.7 mM, 1.3 mM, 1 mM, 0.8 mM, or 0.6 mM. For embodiments in which phosphorous is selected as a limiting nutrient, the limiting concentration of the phosphorous can be, for example, 1.7 mM, 1.3 mM, 1 mM, 0.77 mM, 0.59 mM, 0.45 mM, 0.35 mM, 0.27 mM, 0.2 mM, 0.16 mM, or 0.12 mM. The limiting concentrations are expressed in terms of residual concentrations within a particular one or more reactors of fermentation system. The residual concentration of a chemical is the concentration of the chemical present within the reactor, e.g., at a particular sample time. For embodiments in which the fermentation is operated under continuous conditions, the residual concentration will be a steady-state concentration present within the reactor at all times. For embodiments in which the chemical is fed or otherwise supplied to the reactor, the residual concentration of the chemical is typically different from the feed concentration or supply concentration of the chemical. This difference can be caused by, for example, consumption of the chemical by one or more reactions occurring in the reactor, production of the chemical by one or more reactions occurring in the reactor, or dilution of the chemical by the medium present in the reactor.

In some embodiments, the controlling of the concentration of the selected limiting nutrients includes measuring the residual concentrations of the controlled nutrients. Based on the measured residual concentrations, a feeding of the nutrients to the population can be adjusted so as to maintain the residual concentration within a selected concentration range.

In some embodiments, the controlling of the concentration of the selected limiting nutrients includes measuring the rate of population biomass production in at least one reactor of the fermentation system. Based on the measured biomass production rate, a feeding of the nutrients to the population can be adjusted so as to maintain the ratio of the nutrient feeding rate to the biomass production rate within a selected ratio range.

In some embodiments, the concentration of the selected limiting nutrients in at least one of the fermenters is measured offline by taking periodic samples and submitting said samples for standard analytical measurements such as chromatography and/or spectroscopy. In other embodiments, the concentration of the selected limiting nutrients in at least one of the fermenters is measured by utilizing a sampling port that is coupled to an online measuring apparatus that measures the concentration of the selected limiting nutrient.

In certain aspects the measuring of the limiting nutrient residual concentration, or of the biomass production rate, can include sampling at least one reactor of the fermentation system at a frequency of more than one sample per hour. This relatively high frequency of sampling and measuring is particularly applicable when an online probe or a chromatography column is used to rapidly determine one or more nutrient concentrations. In some embodiments, each occurrence of the measuring corresponds with an occurrence of adjusting the feed rate of the measured limiting nutrient to the reactor accordingly as described in further detail below. In some embodiments, not every occurrence of the measuring corresponds with an adjusting of the feed rate.

In certain aspects, the measuring of the limiting nutrient residual concentration, or of the biomass production rate, can include sampling at least one reactor of the fermentation system at a frequency of fewer than one sample per hour. This relatively low frequency of sampling and measuring is particularly applicable when an offline analytical method, e.g., an enzymatic reaction, is used to determine one of more nutrient concentrations. In some embodiments, each occurrence of the measuring corresponds with an occurrence of adjusting the feed rate of the measured limiting nutrient to the reactor accordingly as described in further detail below. In some embodiments, not every occurrence of the measuring corresponds with an adjusting of the feed rate.

In some embodiments, the present disclosure is also directed to measuring and controlling the limited nutrient in at least one fermenter in which the aerobic biosynthesis occurs. The limiting nutrient feed rate can be controlled to maintain the desired limiting nutrient concentration in the fermenter to produce the desired yield of product. In some embodiments, the reactor system interacts with at least one control loop configured to measure and control limiting nutrient concentration in the fermentation liquid. The control loops can use feed forward controls, feedback controls, and combinations thereof.

In some embodiments, the method further includes operating the fermentation system under continuous fermentation conditions suitable for synthesis of the extracellular product by the organism. By operating the fermentation in a continuous fashion, many shortcomings of alternative batch and fed-batch fermentations can be mitigated or avoided entirely. For example, the discontinuous nature of batch and fed-batch processes inherently include at least some fermentation downtime between cycles, during which the desired fermentations products are not being generated. An important consequence of this downtime is that the productivity of batch and fed-batch processes will be therefore reduced as compared to that of a continuous process. In addition, any operational variability between different cycles of a batch or fed-batch process can impact not only the amount, but also the quality, of the products being generated. This disadvantage is significantly reduced in continuous processes that are configured to operate with constant stead-state conditions.

In certain aspects, the continuous fermentation conditions include concentrations of selected limiting nutrients that are less than their respective limiting concentrations in at least one reactor of the fermentation system. In certain aspects, the continuous fermentation conditions include concentrations of selected limiting nutrients that are less than their respective limiting concentrations in each reactor of the fermentation system.

The continuous fermentation conditions can include, for example, a concentration of nitrogen that is between 0.6 mM and 8.5 mM, e.g., between 0.6 mM and 2.9 mM, between 0.8 mM and 3.8 mM, between 1 mM and 5 mM, between 1.3 mM and 6.5 mM, or between 1.7 mM and 8.5 mM. In terms of upper limits, the continuous fermentation conditions can include a nitrogen concentration less than 8.5 mM, e.g., less than 6.5 mM, less than 5 mM, less than 3.8 mM, less than 2.9 mM, less than 2.3 mM, less than 1.7 mM, less than 1.3 mM, less than 1 mM, or less than 0.8 mM. In terms of lower limits, the continuous fermentation conditions can include a nitrogen concentration that is greater than 0.6 mM, e.g., greater than 0.8 mM, greater than 1 mM, greater than 1.3 mM, greater than 1.7 mM, greater than 2.3 mM, greater than 2.9 mM, greater than 3.8 mM, greater than 5 mM, or greater than 6.5 mM. Higher nitrogen concentrations, e.g., greater than 8.5 mM, and lower nitrogen concentrations, e.g., less than 0.6 mM, are also contemplated.

The continuous fermentation conditions can include, for example, a concentration of phosphorous that is between 0.12 mM and 1.7 mM, e.g., between 0.12 mM and 0.59 mM, between 0.16 mM and 0.77 mM, between 0.2 mM and 1 mM, between 0.27 mM and 1.3 mM, or between 0.35 mM and 1.7 mM. In terms of upper limits, the continuous fermentation conditions can include a phosphorous concentration less than 1.7 mM, e.g., less than 1.3 mM, less than 1 mM, less than 0.77 mM, less than 0.59 mM, less than 0.45 mM, less than 0.35 mM, less than 0.27 mM, less than 0.2 mM, or less than 0.16 mM. In terms of lower limits, the continuous fermentation conditions can include a phosphorous concentration that is greater than 0.12 mM, e.g., greater than 0.16 mM, greater than 0.2 mM, greater than 0.27 mM, greater than 0.35 mM, greater than 0.45 mM, greater than 0.59 mM, greater than 0.77 mM, greater than 1 mM, or greater than 1.3 mM. Higher phosphorous concentrations, e.g., greater than 1.7 mM, and lower phosphorous concentrations, e.g., less than 0.12 mM, are also contemplated.

The continuous fermentation conditions can be such that the carbon in the fermentation is not limiting, e.g., the continuous fermentation conditions can include a carbon concentration greater than the limiting concentration for carbon in at least one reactor of the fermentation system.

An advantage of the method provided herein is that they are capable of producing biomass at a higher yield than typically achieved with continuous fermentation systems and/or limiting nutrient conditions. In some embodiments, the continuous fermentation conditions include a population biomass concentration within a desired steady-state range. The continuous fermentation conditions can include a population biomass concentration that is, for example, between 10 g/L and 100 g/L, e.g., between 10 g/L and 64 g/L, between 19 g/L and 73 g/L, between 28 g/L and 82 g/L, between 37 g/L and 91 g/L, or between 46 g/L and 100 g/L. In terms of upper limits, the population biomass concentration of the continuous fermentation conditions can be less than 100 g/L, e.g., less than 91 g/L, less than 82 g/L, less than 73 g/L, less than 64 g/L, less than 55 g/L, less than 46 g/L, less than 37 g/L, less than 28 g/L, or less than 19 g/L. In terms of lower limits, the population biomass concentration of the continuous fermentation conditions can be greater than 10 g/L, e.g., greater than 19 g/L, greater than 28 g/L, greater than 37 g/L, greater than 46 g/L, greater than 55 g/L, greater than 64 g/L, greater than 73 g/L, greater than 82 g/L, or greater than 91 g/L. Higher concentrations, e.g., greater than 100 g/L, and lower concentrations, e.g., less than 10 g/L, are also contemplated.

In some embodiments, the method further includes maintaining a production rate for the population biomass that is above a targeted level. The biomass production rate can be, for example, between 0.1 g/L/h and 2.5 g/L/h, e.g., between 0.1 g/L/h and 0.69 g/L/h, between 0.14 g/L/h and 0.95 g/L/h, between 0.19 g/L/h and 1.3 g/L/h, between 0.26 g/L/h and 1.8 g/L/h, or between 0.36 g/L/h and 2.5 g/L/h. In terms of upper limits, the biomass production rate can be less than 2.5 g/L/h, e.g., less than 1.8 g/L/h, less than 1.3 g/L/h, less than 0.95 g/L/h, less than 0.69 g/L/h, less than 0.5 g/L/h, less than 0.36 g/L/h, less than 0.26 g/L/h, less than 0.19 g/L/h, or less than 0.14 g/L/h. In terms of lower limits, the biomass production rate can be at least 0.1 g/L/h, e.g., at least 0.14 g/L/h, at least 0.19 g/L/h, at least 0.26 g/L/h, at least 0.36 g/L/h, at least 0.5 g/L/h, at least 0.69 g/L/h, at least 0.95 g/L/h, at least 1.3 g/L/h, or at least 1.8 g/L/h. Higher production rates, e.g., at least 2.5 g/L/h, and lower production rates, e.g., less than 0.1 g/L/h, are also contemplated.

Another advantage of the methods provided herein is that they are capable of producing biomass that includes polyhydroxyalkanoate at a level high enough to provide a nutritional benefit to, for example, an animal feed composition, but low enough to not impact the digestibility of the feed composition or the productivity of the biomass. The concentration of polyhydroxyalkanoate in the population biomass can be, for example, between 5% and 25%, e.g., between 5% and 17%, between 7% and 19%, between 9% and 21%, between 11% and 23%, or between 13% and 25%. In terms of upper limits, polyhydroxyalkanoate concentration in the population biomass can be less than 25%, e.g., less than 23%, less than 21%, less than 19%, less than 17%, less than 15%, less than 13%, less than 11%, less than 9%, or less than 7%. In terms of lower limits, the polyhydroxyalkanoate concentration in the population biomass can be greater than 5%, e.g., greater than 7%, greater than 9%, greater than 11%, greater than 13%, greater than 15%, greater than 17%, greater than 19%, greater than 21%, or greater than 23%. Higher concentrations, e.g., greater than 25%, and lower concentrations, e.g., less than 5%, are also contemplated.

Another advantage of the methods provided herein is that they are capable of maintaining steady-state conditions in which parameters such as the polyhydroxyalkanoate concentration with the biomass are kept at or near a steady-state, improving product homogeneity and process robustness. In some embodiments, the fermentation system is operated and controlled under conditions that produce population biomass having, on average, a polyhydroxyalkanoate concentration that is at or near a target concentration. The desired target polyhydroxyalkanoate concentration can be, for example, 6%, 7.5%, 9%, 10.5%, 12%, 13.5%, 15%, 16.5%, 18%, 19.5%, or 21%. In certain aspects, the relative difference between the target polyhydroxyalkanoate concentration and the average concentration of polyhydroxyalkanoate in the population biomass as measured during any 1 h period of the operating step can be less than 20%, e.g., less than 18.5%, less than 17%, less than 15.5%, less than 14%, less than 12.5%, less than 11%, less than 9.5%, less than 8%, less than 6.5%, or less than 5%. As used herein, the term "relative difference" is defined as the absolute value of the difference between an actual number and a reference number, divide by the reference number. For example, if a target polyhydroxyalkanoate concentration is 15%, and an average measured polyhydroxyalkanoate concentration is 12%, then the relative difference is 20%.

In some embodiments, the polyhydroxyalkanoate of the biomass is polyhydroxybutyrate, polyhydroxyvalerate, or a combination thereof.

In some embodiments, the culturing of the population in the fermentation system includes supplying to the population one or more gases as feedstock components. Non-limiting examples of gases that can be supplied to population include carbon dioxide and hydrogen.

In some embodiments, the culturing of the population in the fermentation system includes supplying to the population one or more sugars as feedstock components. Non-limiting examples of sugars that can be supplied to population include glucose, xylose, and fructose.

In some embodiments, the culturing of the population in the fermentation system includes supplying to the population one or more sugar acids as feedstock components. A non-limiting example of a sugar acid that can be supplied to population is gluconate.

In some embodiments, the culturing of the population in the fermentation system includes supplying to the population one or more carboxylic acids as feedstock components. Non-limiting examples of carboxylic acids that can be supplied to population include propionic acid, lactic acid, formic acid, and lignocellulose-derived levulinic acid.

In some embodiments, the culturing of the population in the fermentation system includes supplying to the population one or more aromatics as feedstock components. Non-limiting examples of aromatics that can be supplied to population include phenol benzoic acid, and lignin-derived compounds such as benzoate analogues.

In some embodiments, the culturing of the population in the fermentation system includes supplying to the population one or more alcohols as feedstock components. Non-limiting examples of alcohols that can be supplied to population include glycerol, methanol, and ethanol.

In some embodiments, the carbon supplied to the population of the organism derives from a biological feedstock. The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles, waste streams from the food processing or dairy industries, or municipal waste such as fruit peel/pulp or whey.

The feedstock source of the carbon supplied to the population can derive, for example, from a food industry waste stream or from an agricultural waste stream. Non-limiting examples of such waste streams include those of a brewing process, a dairy production process, a plant oil production process, an ethanol production process, a sugar production process, a corn processing plant, a soy processing plant, or a fish processing plant. The feedstock source of the carbon supplied to the population can also derive from a byproduct of a food industry process or of an agricultural process. In some embodiments, the carbon is derived from used cooking oil.

In some embodiments, the carbon supplied to the population of the organism derives from a non-biological feedstock. The non-biological feedstock can be, or can derive from, natural gas, syngas, a blend of carbon dioxide and hydrogen, carbon monoxide, hydrogen, oxygen, methanol, ethanol, waste streams from processes to produce monomers for the Nylon-66 and Nylon-6 industries such as but not limited to non-volatile residues (NVRs) or caustic wash waste streams from the cyclohexane oxidation process used to manufacture adipic acid or caprolactam, or waste streams from other chemical industry processes such as, but not limited to processes associated with the carbon black industry, the hydrogen-refining industry, or the petrochemical industry. In some embodiments, the non-biological feedstock is a terephthalic acid (PTA) waste stream.

The method can further include feeding at least one of the selected limiting nutrients to the population. In certain aspects, each of the selected limiting nutrients is fed to the population. The feeding can be performed continuously or intermittently.

In certain aspects, at least one gaseous feed stream is supplied to the population in the fermentation system. The at least one gaseous feed stream can include at least one of the selected limiting nutrients. The at least one gaseous feed stream can include each of the selected limiting nutrients. The at least one gaseous fee stream can include none of the selected limiting nutrients. The fermentation system can be a gas fermentation that includes at least one of natural gas, syngas, carbon monoxide, hydrogen, oxygen, a mixture of carbon dioxide and hydrogen, methanol, ethanol, non-volatile residue, caustic wash from cyclohexane oxidation processes, or a waste stream from a chemical industry such as, but not limited to a carbon black industry, a hydrogen-refining industry, or a petrochemical industry. In one non-limiting embodiment, the gas fermentation comprises carbon dioxide and hydrogen.

In certain aspects, at least one liquid feed stream is supplied to the population in the fermentation system. The at least one liquid feed stream can include at least one of the selected limiting nutrients. The at least one liquid feed stream can include each of the selected limiting nutrients. The at least one feed stream can include none of the selected limiting nutrients. The fermentation system can be a liquid fermentation that utilizes one or more feed components that are fermentable or metabolizable by the organism. Non-limiting examples of feed components include sugars, glycerol, fructose, fatty acids, carboxylic acids, monosaccharides, disaccharides, lignocellulose, hemicellulose, cellulose, lignin, levulinic acid and formic acid, triglycerides, agricultural waste, condensed distillers' solubles or municipal waste, alcohols and/or other soluble components as feedstock. In one non-limiting embodiment, the feedstock for liquid fermentation is derived from lower value by-products or waste-products from commercial operations. In one non-limiting embodiment, the feedstock for liquid fermentation is derived from ethanol thin stillage stream. In one non-limiting embodiment, the feedstock for liquid fermentation is derived from cooking oil.

The methods can further include recovering biomass from the fermentation system. Once the population biomass has been generated, any suitable technique generally known in the art can be used to isolate the biomass from the system. In some embodiments, the cell membrane of the organism is broken down via lysis to improve the availability of protein to the animal consuming the biomass or an animal feed derived therefrom. Either mechanical or chemical lysis can be used.

Also provided are animal feeds that include biomass generated by the methods disclosed herein. The terms "feed" or "feed composition" or "feed additive", as used herein, refer to any compound, preparation, mixture or composition suitable for, or intended for, intake by an animal. The term "animal" includes all animals including human. Examples of animals are non-ruminants, and ruminants. Ruminant animals include, for example, animals such as sheep, goat, and cattle, e.g. cow such as beef cattle and dairy cows. The animal can also be a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

In some embodiments, the biomass provided herein provides the animal feed with a higher concentration of amino acid(s), oligopeptides, polypeptides or derivatives thereof, as compared to an animal feed composition not having the provided biomass. In certain aspects, the biomass provides the animal feed with a higher amount of protein as compared to an animal feed composition not having the provided biomass. In certain aspects, the biomass provides the animal feed with an amount of polyhydroxyalkanoate that is between 5% and 25%.

In one non-limiting embodiment, the biomass is incorporated into the animal feed at greater than 10% by weight of the animal feed. In another non-limiting embodiment, the biomass is incorporated into the animal feed at greater than 20% by weight of the animal feed. In yet another non-limiting embodiment, the biomass is incorporated into the animal feed at greater than 30% by weight of the animal feed.

The following embodiments are contemplated. All combinations of features and embodiments are contemplated.

Embodiment 1

A method for producing a biomass in a fermentation system, the method comprising: providing an organism belonging to a genus selected from the group consisting of *Cupriavidus* and *Ralstonia*; culturing a population of the organism in the fermentation system; independently controlling the concentration of each of one or more selected limiting nutrients in at least one reactor of the fermentation system, wherein the selected limiting nutrients comprise nitrogen, phosphorous, or a combination thereof; and operating the fermentation system under continuous fermentation conditions comprising a nitrogen concentration between 1 mM and 5 mM in at least one reactor of the fermentation system and/or a phosphorous concentration between 0.2 mM and 1 mM in the at least one reactor; and maintaining a population biomass production rate of at least 0.5 g/L/h in the at least one reactor, wherein the population biomass comprises between 5 wt % and 25 wt % polyhydroxyalkanoate.

Embodiment 2

An embodiment of embodiment 1, wherein the average concentration of polyhydroxyalkanoate in the population biomass as measured during any 1 h period of the operating step is within 20% of a target polyhydroxyalkanoate concentration.

Embodiment 3

An embodiment of embodiment 1 or 2, wherein the continuous fermentation conditions further comprise a concentration of carbon greater than its limiting concentration in the at least one reactor.

Embodiment 4

An embodiment of embodiment 3, wherein the carbon derives from a biological feedstock.

Embodiment 5

An embodiment of embodiment 3, wherein the carbon derives from a non-biological feedstock.

Embodiment 6

An embodiment of embodiment 4 or 5, wherein the feedstock derives from a food industry waste stream or an agricultural industry waste stream.

Embodiment 7

An embodiment of any of the embodiments of embodiment 1-6, wherein the culturing further comprises supplying to the population one or more gaseous feed streams.

Embodiment 8

An embodiment of any of the embodiments of embodiment 1-7, wherein the culturing further comprises supplying to the population one or more liquid feed streams.

Embodiment 9

An embodiment of any of the embodiments of embodiment 1-8, wherein the culturing further comprises supplying to the population one or more feedstocks selected from the list consisting of gases, sugars, sugar acids, carboxylic acids, aromatics, and alcohols.

Embodiment 10

An embodiment of embodiment 9, wherein the gases are selected from the group consisting of carbon dioxide and hydrogen; wherein the sugars are selected from the group consisting of glucose, xylose, and fructose; wherein the sugar alcohols consist of gluconate; wherein the carboxylic acids are selected from the group consisting of propionic acid, lactic acid, and formic acid; wherein the aromatics are selected from the group consisting of phenol and benzoic acid; and wherein the alcohols consist of glycerol.

Embodiment 11

An embodiment of any of the embodiments of embodiment 1-10, wherein the continuous fermentation conditions further comprise a population biomass concentration between 10 g/L and 50 g/L.

Embodiment 12

An embodiment of any of the embodiments of embodiment 1-11, wherein the fermentation system comprises a single stage continuous stirred tank reactor.

Embodiment 13

An embodiment of any of the embodiments of embodiment 1-12, wherein the culturing comprises feeding at least one of the selected limiting nutrients to the population, wherein the feeding is performed continuously.

Embodiment 14

An embodiment of any of the embodiments of embodiment 1-12, wherein the culturing comprises feeding at least one of the selected limiting nutrients to the population, wherein the feeding is performed intermittently.

Embodiment 15

An embodiment of embodiment 13 or 14, wherein the controlling comprises measuring the residual concentration of the at least one selected limiting nutrient in the at least one reactor and adjusting the feeding of the at least one selected limiting nutrient to maintain the residual concentration within a selected concentration range.

Embodiment 16

An embodiment of embodiment 15, wherein the measuring of the residual concentration comprises sampling the at least one reactor at a frequency of greater than one sample per hour.

Embodiment 17

An embodiment of embodiment 15, wherein the measuring of the residual concentration comprises sampling the at least one reactor at a frequency of less than one sample per hour.

Embodiment 18

An embodiment of any of the embodiments of embodiment 15-17, wherein the measuring comprises sampling through a port coupled to an online measuring apparatus.

Embodiment 19

An embodiment of embodiment 13 or 14, wherein the controlling comprises measuring the rate of population biomass production in the at least one reactor and adjusting the feeding of the at least one selected limiting nutrient to maintain the ratio of the rate of feeding to the rate of population biomass production within a selected ratio range.

Embodiment 20

An embodiment of any of the embodiments, of embodiment 15-19, wherein the measuring and the adjusting comprise operating a control loop, wherein the control loop uses feedback control, feed forward control, or a combination thereof.

Embodiment 21

An embodiment of any of the embodiments of embodiment 1-20, wherein the polyhydroxyalkanoate comprises polyhydroxybutyrate, polyhydroxyvalerate, or a copolymer thereof.

Embodiment 22

An embodiment of any of the embodiments of embodiment 1-21, wherein the organism is selected from the group consisting of *Cupriavidus necator, Cupriavidus metallidurans, Cupriavidus taiwanensis, Cupriavidus pinatubonensis, Cupriavidus basilensis,* and *Ralstonia pickettii*.

Embodiment 23

A biomass produced using the method of an embodiment of any of the embodiments of embodiment 1-22.

Embodiment 24

An animal feed comprising the biomass of embodiment 23.

EXAMPLES

The present disclosure will be better understood in view of the following non-limiting examples.

Example 1. Nitrogen Limitation Promoting PHB Production in *C. necator* H16

*C. necator* H16 was grown on a fructose based medium with ammonium sulphate as a source of nitrogen. Continuous culture was used to compare four different steady state conditions, each with a different concentration of fed ammonium sulphate (incrementally lowered in order to examine nitrogen limitation). Growth was established at a dilution rate of $D=0.1$ $h^{-1}$, a temperature of 30° C. and a pH of 6.6 in a volume maintained at 0.8 L. Three replicate vessels were run for each strain, and two samples were taken under each steady state, resulting in six data points used to establish a mean and standard deviation. For each steady state, concentrations were measured of biomass (dry cell weight and OD600), residual nitrogen and carbon, and PHB (microscopy and empirical determination via gas chromatography). Oxygen uptake rate (OUR) and carbon dioxide emission rate (CER) were also determined.

From the data presented in Table 1, it can be seen that dry cell weight values decreased with increasing nitrogen limitation. In addition, *C. necator* H16 cell weights were greater than those of the PHB null mutant, likely due in part to the accumulation of PHB. Overlapping standard deviations between the two strains made the effect of PHB on cell weight difficult to discriminate. This was also true for biomass determination by OD600, as PHB appeared to contribute significantly to absorbance at 600 nm by the H16 cultures.

CER and OUR were both found to decrease as the amount of ammonium sulphate in the feed was also decreased. The respiratory quotient (RQ, defined as the quotient CER/OUR) was fractionally higher for *C. necator* H16 at the lower feeding concentrations (data not shown). The productivity of PHB, in terms of grams of PHB per liter of culture per hour, was shown to increase with increasing limitation of nitrogen, up to a maximum value of 0.35 g/L/h (Table 1). All carbon mass balances closed to an acceptable percentage in the experiments.

TABLE 1

PHB production in *C. necator* H16 under nitrogen limitation at D = 0.1 h$^{-1}$

| | | | | |
|---|---|---|---|---|
| Ammonium sulphate feed concentration (g/L) | 14 | 7 | 3.5 | 1.75 |
| Nitrogen feed rate (mM/h) | 10.8 | 5.4 | 2.7 | 1.3 |
| Residual NH$_3$ concentration (mM) | >6 | 2.9 | 1.8 | — |
| Dry cell weight concentration (g/L) | 19.29 | 18.30 | 14.44 | 11.40 |
| Average PHB concentration (%) | 2.2 | 12.1 | 22.4 | 30.9 |
| PHB concentration (g/L) | 0.42 | 2.21 | 3.23 | 3.52 |
| Non-PHB cell mass concentration (g/L) | 18.87 | 16.09 | 11.21 | 7.89 |
| Total biomass productivity (g/L/h) | 1.93 | 1.83 | 1.44 | 1.14 |
| PHB productivity (g/L/h) | 0.04 | 0.22 | 0.32 | 0.35 |
| Non-PHB cell mass productivity (g/L/h) | 1.89 | 1.61 | 1.12 | 0.79 |

Example 2. Phosphate Limitation Promoting PHB Production in *C. necator* H16

*C. necator* H16 was grown on a fructose based medium with ammonium sulphate as a source of nitrogen. Continuous culture was used to compare four different steady states, each with a different concentration of fed phosphate compounds (made up of 60 wt % potassium dihydrogen and 30 wt % disodium phosphates, incrementally lowered in order to examine phosphate limitation). Growth was established at a dilution rate of $D=0.05$ $h^{-1}$, a temperature of 30° C., and a pH of 6.6 in a volume maintained at 0.8 L. Four replicate vessels were run for each strain, and a sample was taken under each steady state, resulting in four data points used to establish a mean and standard deviation. For each steady state, concentrations were measured of biomass (dry cell weight and OD600), residual carbon, and PHB (microscopy and empirical determination via GC). OUR and CER were also determined.

Although residual phosphate concentration was not determined empirically, when fed with a phosphate concentration of 1 g/L the media was designed, by elevating the mass of carbon and nitrogen by 50%, for this component to be the limiting factor. This determination was based on weights calculated from an elemental analysis of the biomass. Biomass was shown to decrease with increased phosphate limitation, although the simultaneous accumulation of PHB contributed to both OD600 readings and cell weight, made discrimination of cell growth and PHB accumulation difficult (Table 2).

The accumulation of PHB under the greatest limitation was determined to be as great as 18% of the cell mass A rapid qualitative method, via Nile red staining of cells, demonstrated that PHB was being accumulated in a significant quantity of the cells (data not shown).

CER and OUR were both found to decrease as the amount of phosphate in the feed was also decreased. RQ was fractionally higher for *C. necator* H16 at the lower feeding concentrations (data not shown). The productivity of PHB followed a similar trend to that of the PHB yield data, reaching a peak at 0.24 g/L/h. All carbon mass balances closed to greater than 87% in the experiments.

TABLE 2

PHB production in *C. necator* H16 under phosphate limitation at $D = 0.05$ $h^{-1}$

| | | | | |
|---|---|---|---|---|
| KH$_2$PO$_4$ feed concentration (g/L) | 1.41 | 0.71 | 0.35 | 0.17 |
| Na$_2$HPO$_4$ feed concentration (g/L) | 0.94 | 0.47 | 0.24 | 0.12 |
| Phosphorous feed rate (mM/h) | 17.0 | 8.5 | 4.3 | 2.1 |
| Dry cell weight concentration (g/L) | 25.0 | 26.3 | 21.4 | 12.4 |
| Average PHB concentration (%) | 4.5 | 18.2 | 13.3 | 5.1 |
| PHB concentration (g/L) | 1.12 | 4.79 | 2.85 | 0.63 |
| Non-PHB cell mass concentration (g/L) | 23.84 | 21.54 | 18.57 | 11.72 |
| Total biomass productivity (g/L/h) | 1.25 | 1.32 | 1.07 | 0.62 |
| PHB productivity (g/L/h) | 0.06 | 0.24 | 0.14 | 0.03 |
| Non-PHB cell mass productivity (g/L/h) | 1.19 | 1.08 | 0.93 | 0.59 |

While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only and is not intended to limit the disclosure. All patents and publications cited herein are incorporated by reference in their entirety.

We claim:

1. A method for producing a biomass in a continuous fermentation system; the method comprising:
    providing an organism belonging to a genus selected from the group consisting of *Cupriavidus* and *Ralstonia*;
    culturing a population of the organism to produce a biomass comprising polyhydroxyalkanoate, in the fermentation system;
    independently controlling a concentration of each of one or more selected limiting nutrients in at least one reactor of the fermentation system, wherein the selected limiting nutrients comprise nitrogen; phosphorous; or a combination thereof; and
    operating the fermentation system under continuous fermentation conditions comprising a limiting nitrogen concentration of 0.6 mM to 2.9 mM in at least one reactor of the fermentation system and/or a limiting phosphorous concentration of 0.12 mM to 1.7 mM in the at least one reactor; and
    maintaining a population biomass production rate of at least 0.5 g/L/h in the at least one reactor and measuring a concentration of polyhydroxyalkanoate, wherein the population biomass comprises a targeted concentration of between 5 wt % and 25 wt % polyhydroxyalkanoate, wherein a relative difference between the targeted concentration of polyhydroxyalkanoate in the population biomass and an average concentration of polyhydroxyalkanoate in the population biomass as measured during a 1 hour period during operation of the fermentation system is less than 20%.

2. The method of claim 1, wherein the continuous fermentation conditions further comprise a concentration of carbon greater than a limiting concentration of the carbon in the at least one reactor.

3. The method of claim 2, wherein the carbon derives from a biological feedstock.

4. The method of claim 2, wherein the carbon derives from a non-biological feedstock.

5. The method of claim 3, wherein the feedstock derives from a food industry waste stream or an agricultural industry waste stream.

6. The method of claim 1, wherein the culturing further comprises supplying to the population one or more gaseous feed streams.

7. The method of claim 1, wherein the culturing further comprises supplying to the population one or more liquid feed streams.

8. The method of claim 1, wherein the culturing further comprises supplying to the population one or more feedstocks selected from the list consisting of gases, sugars, sugar acids, carboxylic acids, aromatics, and alcohols.

9. The method of claim 8, wherein when supplied the gases are selected from the group consisting of carbon dioxide and hydrogen; wherein when supplied the sugars are selected from the group consisting of glucose, xylose, and fructose; wherein when supplied the sugar acids consist of gluconate; wherein when supplied the carboxylic acids are selected from the group consisting of propionic acid, lactic acid, and formic acid; wherein when supplied the aromatics are selected from the group consisting of phenol and benzoic acid; and wherein when supplied the alcohols consist of glycerol.

10. The method of claim 1, wherein the continuous fermentation conditions further comprise a population biomass concentration between 10 g/L, and 50 g/L.

11. The method of claim 1, wherein the fermentation system comprises a single stage continuous stirred tank reactor.

12. The method of claim 1, wherein the culturing comprises feeding at least one of the selected limiting nutrients to the population; and wherein the controlling comprises:
   measuring the residual concentration of the at least one selected limiting nutrient in the at least one reactor, and
   adjusting the feeding of the at least one selected limiting nutrient to maintain the residual concentration within a selected concentration range.

13. The method of claim 12, wherein the measuring of the residual concentration comprises sampling the at least one reactor at a frequency of more than one sample per hour.

14. The method of claim 12, wherein the measuring of the residual concentration comprises sampling the at least one reactor at a frequency of fewer than one sample per hour.

15. The method of claim 12 wherein the measuring comprises sampling through a port coupled to an online measuring apparatus.

16. The method of claim 1, wherein the culturing comprises feeding at least one of the selected limiting nutrients to the population, and wherein the controlling comprises:
   measuring the rate of population biomass production in the at least one reactor, and
   adjusting the feeding of the at least one selected limiting nutrient to maintain the ratio of the rate of feeding to the rate of population biomass production within a selected ratio range.

17. The method of claim 1, wherein the organism is selected from the group consisting of *Cupriavidus necator, Cupriavidus metallidurans, Cupriavidus taiwanensis, Cupriavidus pinatubonensis, Cupriavidus basilensis*, and *Ralstonia pickettii*.

18. The method of claim 12, wherein feeding the selected limiting nutrients is performed continuously or intermittently.

* * * * *